(12) United States Patent
Dahlor et al.

(10) Patent No.: US 12,257,129 B1
(45) Date of Patent: Mar. 25, 2025

(54) THERAPY TAPE HAVING TRANSDERMAL DELIVERY FEATURES

(71) Applicants: Frank Dahlor, Monterey, CA (US); Nelson Thomas Rivera, Seaside, CA (US)

(72) Inventors: Frank Dahlor, Monterey, CA (US); Nelson Thomas Rivera, Seaside, CA (US)

(*) Notice: Subject to any disclaimer, the term of this patent is extended or adjusted under 35 U.S.C. 154(b) by 1146 days.

(21) Appl. No.: 16/987,333

(22) Filed: Aug. 6, 2020

Related U.S. Application Data

(60) Provisional application No. 62/883,623, filed on Aug. 6, 2019.

(51) Int. Cl.
| | |
|---|---|
| *A61F 13/00* | (2024.01) |
| *A61F 13/02* | (2024.01) |
| *A61H 7/00* | (2006.01) |
| *A61H 9/00* | (2006.01) |
| *A61K 9/70* | (2006.01) |
| *A61K 31/05* | (2006.01) |
| *A61K 31/352* | (2006.01) |
| *A61N 1/04* | (2006.01) |
| *A61H 23/02* | (2006.01) |

(52) U.S. Cl.
CPC .... *A61F 13/00063* (2013.01); *A61F 13/0236* (2013.01); *A61H 7/007* (2013.01); *A61K 9/7084* (2013.01); *A61K 31/05* (2013.01); *A61K 31/352* (2013.01); *A61H 9/005* (2013.01); *A61H 23/02* (2013.01); *A61H 2201/0153* (2013.01); *A61H 2201/105* (2013.01); *A61H 2201/1253* (2013.01); *A61N 1/0456* (2013.01)

(58) Field of Classification Search
CPC ......... A61H 7/007; A61F 5/0104; A61F 5/40; A61K 9/06; A61K 9/703; A61K 31/05; A61K 31/352
See application file for complete search history.

(56) References Cited

U.S. PATENT DOCUMENTS

| | | | | |
|---|---|---|---|---|
| 6,113,940 | A | * | 9/2000 | Brooke ................ A61K 9/7084 424/448 |
| 10,350,133 | B2 | | 7/2019 | Dahlor |
| 2002/0094998 | A1 | | 7/2002 | Burke |
| 2002/0156423 | A1 | | 10/2002 | Tollini |
| 2002/0193724 | A1 | | 12/2002 | Stebbings |

(Continued)

*Primary Examiner* — Jianfeng Song

(57) ABSTRACT

A therapy device having transdermal and/or topical delivery features to treat myofascial and/or musculoskeletal tissue imbalances and/or treat inflammation. The therapy device is comprised of a soft tissue mobilizing device having a front surface, and a back surface having transdermal delivery features. The back surface includes a therapeutic substance disposed thereon and an adhesive to adhere the device directly to the soft tissue area of a user's body where muscle tension, aches and pain are present. The device when applied decompresses the soft tissue area being treated. The front surface includes a gripping mechanism to allow the user to grip the mechanism to manually lift and shift the soft tissue area being treated. The transdermal delivery features of the device and the manual lifting and shifting of the user's soft tissue reduces the time period for normalizing the myofascial and/or musculoskeletal tissue area being treated.

18 Claims, 31 Drawing Sheets

(56) References Cited

U.S. PATENT DOCUMENTS

| | | | |
|---|---|---|---|
| 2010/0119586 A1* | 5/2010 | Dupont | A61K 9/7084 |
| | | | 424/449 |
| 2015/0297556 A1* | 10/2015 | Smith | A61K 47/08 |
| | | | 424/449 |
| 2015/0313788 A1 | 11/2015 | Conte | |
| 2016/0184172 A1* | 6/2016 | Dahlor | A61H 7/001 |
| | | | 601/84 |
| 2017/0181830 A1* | 6/2017 | Felix | A61F 2/0063 |

* cited by examiner

Medical Benefits of Various Cannabinoids

Medical Benefits of Various Cannabinoids (continued)

Medical Benefits and Effects of Various Terpenes

Medical Benefits and Effects of Various Terpenes (continued)

THERAPY TAPE HAVING TRANSDERMAL DELIVERY FEATURES

PRIORITY CLAIM

This application claims priority to U.S. provisional application 62/883,623, entitled "Therapy Tape Having Transdermal Delivery Features", filed on Aug. 6, 2019.

INCORPORATION BY REFERENCE

This application incorporates by reference the disclosures of U.S. Pat. No. 10,350,133 filed on Jul. 17, 2015, and Appl. No. 62/834,942 filed on Apr. 16, 2019, as if fully set forth herein.

TECHNICAL FIELD

The present invention relates to the field of treating soft tissue imbalances, and more particularly, but not limited to, a mobilizing device having transdermal delivery features for treating myofascial and/or musculoskeletal imbalances and inflammation in mammals.

BACKGROUND OF THE INVENTION

An important area of a mammal's and/or person's body that is often overlooked and/or overlooked while treating injuries is the musculoskeletal system and myofascial tissue. The musculoskeletal system includes the connection of muscles with the skeleton, spine, brain and the connective tissues bridging these organs and structures together. Myofascial tissue pertains to the fibrous tissues called fascia (i.e., soft tissue) that encloses and separates layers of muscle. Further, muscles and their connective tissue connect different portions of the skeleton from the top of the head down through the torso and all the way to the feet.

Myofascial and/or musculoskeletal injuries can occur in a variety of ways. Accidents, falls, poor body mechanics, sport injuries, poor posture, stress from everyday activities, tension, improper exercise regiments, and age-related degeneration relate to some of the factors that can cause these types of injuries directly or indirectly. When a mammal's body such as a human's body is adversely affected by a soft tissue injury (i.e., myofascial and/or musculoskeletal) the body's central nervous system, which consists of the brain and spinal cord, receives a pain message that is detected by nerve receptors called nociceptors.

After the body's central nervous system receives a pain signal, it attempts to protect the injured location by sending a signal to the surrounding muscle area to guard itself and sustain a static position to avoid shear force. The surrounding muscle is forced to work harder to protect the injured area, which produces tensional imbalances on the body tissue of the musculoskeletal system which can create contracture/compression on such tissue causing the systems of the body to decalibrate from their naturally balanced state. A contracture is the shortening of soft tissue and could occur in a muscle, tendon, ligament, or fasciae.

If the musculoskeletal system and/or soft tissue injury locations are left unattended, the connective tissue will progressively contract, stick or glue to itself even when the connected muscle is stretched. Contracted connective tissue can therefore contribute to decalibration of the musculoskeletal system from its natural state causing tensional imbalances. As an imbalance occurs in one area of the body, the contracture of muscular and connective tissues imparts similar imbalances in the surrounding areas. What can occur then is a chain reaction of tissue contractions that can spread from a single point to several points along the length of the body perpetuating imbalances throughout the body.

The result of tensional imbalances related to soft tissue injuries can often manifest themselves as physical pain. In order to break the pain cycle, an external intervention must be introduced to stimulate release of these tensional imbalances, in order to decrease muscle tension. Currently, one type of therapy used to treat myofascial and musculoskeletal imbalances and/or tension is myofascial release therapy.

Therapeutic treatment to aid patients' recovery from bodily injuries (e.g., strained, damaged, or weakened muscles, torn and/or strained ligaments, bruising, and/or the like) and/or medical procedures (e.g., surgical procedures, such as joint replacement), and/or to minimize patient discomfort from disabilities and/or other conditions (e.g., Fibromyalgia, Multiple Sclerosis (MS), and/or the like) involves professional-guided treatment sessions (e.g., under the guidance of a physician, physical therapist, and/or the like) and/or patient-guided treatment sessions (e.g., self-guided exercises) that may be prescribed by the overseeing professional. While the professional-guided treatment sessions may involve an exercise portion in which the patient performs exercises similar to those included in the patient-guided treatment sessions, professional-guided treatment sessions may include additional therapeutic massage and/or manipulation sessions in which the professional manipulates the patient's body at or near the injury site in order to stimulate blood flow, minimize scar tissue formation, encourage muscle growth, and/or the like.

Myofascial release is a form of soft tissue therapy used to treat somatic dysfunction and the resultant pain and restriction of motion in a patient/mammal. The direct myofascial release (or deep tissue work) method engages the myofascial tissue (tension). The tissue is loaded with a constant force until release occurs which can leave the treated soft tissue area of the patient/mammal sore and/or in pain based on the attempt to normalize the soft tissue area. Further, practitioners also use knuckles, elbows, forearm or other compressive tools, massage heads and postural tapes to slowly stretch the restricted fascia by applying a few kilograms of force or tens of newtons. Direct myofascial release is an attempt to bring about changes in the myofascial structures by stretching or elongation of fascia or mobilizing adhesive tissues.

Indirect mmyofascial release involves a gentle stretch, with only a few grams of pressure, which allows the fascia to 'unwind' itself but can still leave the treated area sore. The dysfunctional tissues are guided along the path of least resistance until free movement is achieved. Moreover, this technique involves a slow stretch of the fascia until reaching a barrier and/or restriction. As the barrier and/or restrictions releases, the hand will feel the motion and softening of the tissue. They key to this technique is sustained pressure over time. However, the unwinding and/or normalizing of the dysfunctional fascia/soft tissue over time can leave a patient in discomfort or pain during the healing and normalizing process.

Postural or prosthetic tapes and/or transdermal type tapes are used to treat myofascial and/or musculoskeletal conditions by applying these tapes directly to the affected area. These types of tapes will remain on the affected area for a select amount of time to bring myofascial and/or musculoskeletal tissue back to normal. This technique is passive because the tape remains on the affected area without any further manipulation of the tape. In fact, one problem associated with this technique is that it does not allow a physical therapist and/or patient to lift and/or shift the tape by hand in order to speed up the process of bringing the myofascial and/or musculoskeletal tissue back to normal.

Currently, there are tapes available that allow a patient and/or a physical therapist to lift and shift the tape with a tab in order to help normalize and speed up the process of bringing the myofascial and/or musculoskeletal tissue back to normal. However, the available mobilizing tapes on the market do not include a mobilizing device having at least one transdermal receiving pad for treating the myofascial and/or musculoskeletal imbalances in mammals with at least one therapeutic substance. Importantly, these tapes do not include a transdermal mobilizing device that utilizes cannabinoids and/or CBD derived from citrus (e.g., orange and lemon peel), hops and tree bark (e.g., evergreen tree). Accordingly, one purpose of the present invention is to extend the widespread potential therapeutic benefits and/or transdermal use of cannabinoids, CBD or other healing gels/ointments. These healing gels/ointments can include therapeutic substances to relieve and/or reduce inflammation and pain. The chemical composition and active ingredients of *cannabis* and CBD allow for its transdermal delivery as a dietary supplement or as a medicinal substance.

*Cannabis* legalization in several jurisdictions in the United States has led to strong demand for products that include oils and chemical compounds extracted from *cannabis* such as cannabinoids used by individuals without smoking the plant itself. For example, demand has grown in the areas of Pharmaceuticals commonly referred to as "medical marijuana," and in nutritional supplements, edible products, beverages, vaporizer fluids, and transdermal products to just name a few.

In light of the shortcomings in the prior art, there is a need for a transdermal soft tissue mobilizing device having at least one transdermal therapeutic receiving pad to replace outdated postural and/or prosthetic tapes. This new device also includes transdermal delivery features and a tab gripping mechanism for allowing a physical therapist, patient, trainer or the like to lift and shift the device by hand via a flossing (i.e., pulling, shifting, stretching) motion to speed up the time period of bringing myofascial and/or musculoskeletal tissue back to normal in mammals and/or persons. The tab gripping mechanism can also be removable.

BRIEF SUMMARY OF THE INVENTION

Various embodiments are directed to a therapy tape having transdermal features (e.g., a therapy tape, physiotherapy tape, physical therapy tape, chiropractic therapy tape, naprapathy therapy tape, massage therapy tape, lymphatic therapy tape, sports therapy tape, and/or the like) having one or more handles and/or one or more stimulators configured to enable a patient to continue manipulation and/or massage based treatment without the supervision of a medical professional. For example, the patient may be able to lift and/or move portions of the patient's skin to encourage rehabilitation and/or healing of portions of the patient's body onto which the tape has been secured. Likewise, the therapy tape may be configured to aid in treatment of strained, damaged, and/or weakened muscles and/or ligaments, hematoma, bruising, cording, spinal injuries, numbness, tissue and/or muscle tension and/or stiffness (e.g., from spasticity). The therapy tape may additionally be configured to aid in treatment of various bodily conditions, such as epicondylitis, plantar fasciitis, MS, fibromyalgia, swelling lymphedema, lipedema, and/or the like. In various embodiments, the therapy tape may be configured to provide treatment to prevent injury, to aid in comfort of the patient, and/or the like. For instance, the therapy tape may be configured to trigger acupuncture points, pressure points, and/or the like. The therapy tape may additionally be configured to lift, stretch, and/or move tissue and/or anchor filaments connected with the tissue. The therapy tape may also be configured to provide support to various bodily portions (e.g., a limb), and/or the like. The therapy tape may be usable with adults, children, elderly patients, and/or the like. The one or more handles are removable in various embodiments.

Accordingly, various embodiments are directed to a therapy tape comprising (i) a backing layer having transdermal features that is configured to conform to a portion of a patient's body, wherein the flexible backing layer defines a top side and a bottom side opposite the top side; (ii) an adhesive material secured relative to the bottom side of the flexible backing layer, wherein the adhesive material is configured to adhere the backing layer against a patient's skin; and (iii) one or more handles secured relative to the top side of the flexible backing layer, wherein the one or more handles are secured to the flexible backing layer via one or more fasteners. The transdermal features are configured to aid in the healing process when using the device. In certain embodiments, the adhesive material is configured to maintain adherence with the backing layer and the patient's skin while the handles are pulled normal to the patient's skin. In various embodiments, the adhesive material is secured to the backing layer such that the adhesive material and the backing layer do not substantially delaminate upon removal from the patient's skin.

In various embodiments, the backing layer is inelastic. The adhesive material and the transdermal substance(s) may be heat activated by the patient's body heat. In certain embodiments, the one or more fasteners comprise a second adhesive material different from said adhesive material, wherein the second adhesive material is configured to permanently secure the one or more handles relative to the top side of the flexible backing layer. In certain embodiments, the one or more handles comprise a base portion configured to be secured onto the top side of the backing layer and a grip portion extending away from the base portion. In various embodiments, the base portion of the one or more handles are secured relative to the top side of the backing layer via the one or more fasteners. In other embodiments, the one or more handles are removable.

In various embodiments, the backing layer defines a length and a width measured perpendicular to the length, wherein the length is substantially longer than the width. In various embodiments, at least one of the one or more handles extends across the backing layer in a direction parallel with the width of the backing layer. In alternative embodiments, at least one of the one or more handles extends across the backing layer in a direction parallel with the length of the backing layer. In various embodiments, the one or more handles are detachably secured relative to the backing layer, and wherein the one or more fasteners are selected from: magnets, hook-and-loop fasteners, or snap-fasteners.

In various embodiments, the therapy tape additionally comprises one or more stimulators configured to apply a stimulating signal to a patient's skin and/or to the transdermal features of the present invention. The one or more stimulators may comprise at least one of: a vibration element, a pressure applicator, or a TENS device. Moreover, the therapy tape may comprise a controller configured to generate one or more stimulator signals to selectively activate the one or more stimulators and/or the transdermal substance(s); wherein the controller comprises at least one communication interface configured to receive data transmitted from at least one external computing entity. In certain embodiments, the communication interface is a wireless communication interface.

Various embodiments are directed to a method for manipulating a flexible material (e.g., skin). The method may comprise steps for: (i) securing a tape structure against a surface of the flexible material, wherein the tape structure comprises: a backing layer configured to conform to a portion of the surface of the flexible material, wherein the flexible backing layer defines a top side and a bottom side opposite the top side; an adhesive material secured relative to the bottom side of the flexible backing layer, wherein the adhesive material is configured to adhere the backing layer against the surface of the flexible material; and one or more handles secured relative to the top side of the flexible backing layer, wherein the one or more handles are secured to the flexible backing layer via one or more fasteners; and (ii) applying a tensile force to at least one of the one or more handles to lift a portion of the backing layer and a secured portion of the surface of the flexible material.

In various embodiments of the present invention, the one or more handles are detachably secured relative to the top side of the flexible backing layer, and accordingly the method may further comprise steps for securing one or more handles relative to the top side of the flexible backing layer via one or more detachable fasteners. Moreover, in various embodiments, the adhesive material is heat activated, and accordingly the steps for securing the tape structure against a surface of the flexible material may comprise: placing the adhesive material of the tape structure against the patient's skin; and raising the temperature of the adhesive material based on the patient's body heat to securely adhere the adhesive material to the patient's skin and/or activate the transdermal features of the present invention. Further, in certain embodiments, the backing material is inelastic, such that applying a tensile force to at least one of the one or more handles causes at least a portion of the surface of the flexible material to displace in a direction of the tensile force by a distance at least substantially equal to a displacement of a handle.

In various embodiments, the transdermal substance(s) will be comprised of substances having features to reduce inflammation, wherein a user does not have to use ingestible medicines and/or substances to relieve and/or reduce inflammation. This will also allow a person to possibly avoid stomach irritation from said medicine and/or avoid ulcers, bleeding, or holes in the stomach or intestine. These problems may develop at any time during treatment, which may happen without warning symptoms, and may cause death.

Consequently, for a better understanding of the present invention, its functional advantages and the specific benefits attained by its uses, reference should be made to the drawings, claims and descriptive matter in which there are illustrated embodiments of the present invention.

DETAILED DESCRIPTION OF THE INVENTION

Introduction

Figure 1A:
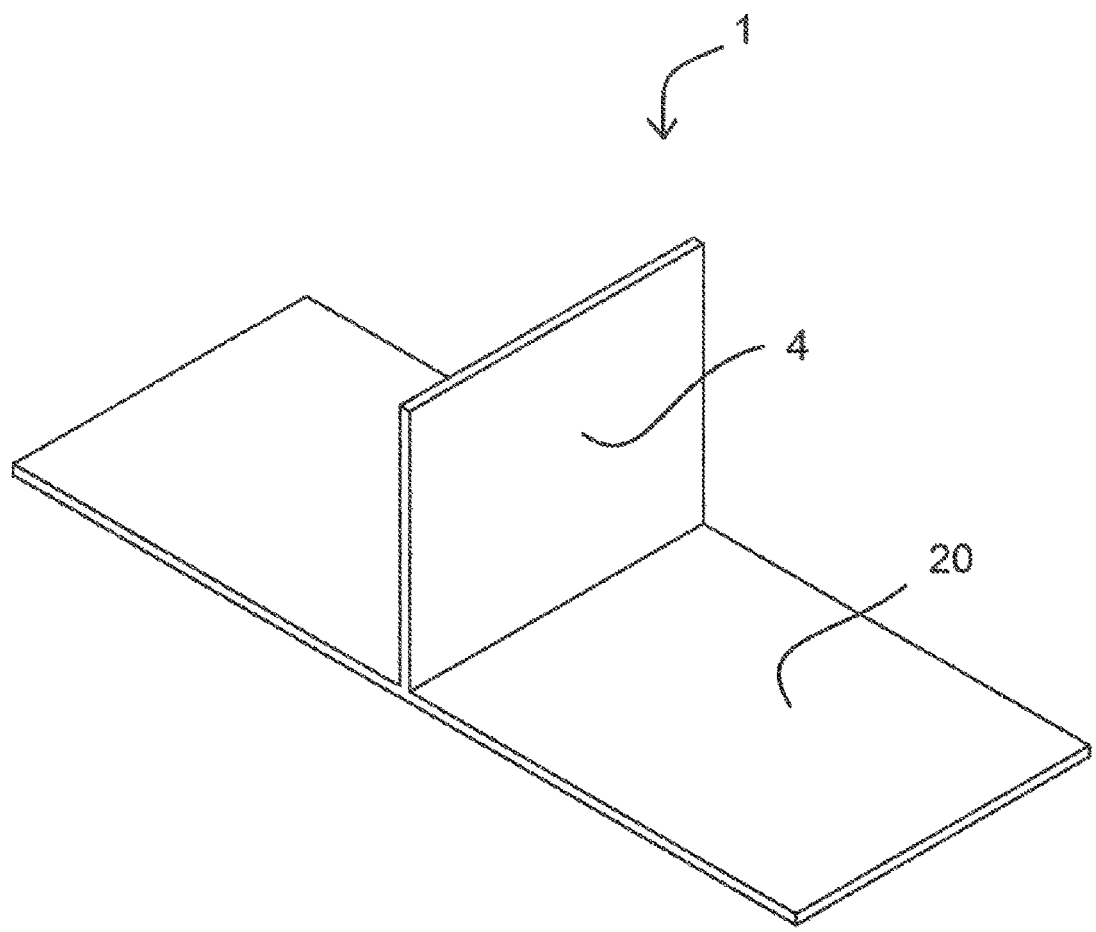
FIGS. 1A-1C show various embodiments of therapy tape.

The following detailed description is of the best currently contemplated modes of carrying out various embodiments of the invention in which said embodiments can be carried out independently and/or in combination. The description is not to be taken in a limiting sense but is made for at least the purpose of illustrating the general principles of the invention, since the scope of the invention is best defined by the appended claims.

a. *Cannabis* and Cannabinoids

*Cannabis* is a flowering plant that includes three species or sub-species, namely *sativa*, indica and *ruderalis*. The plant is indigenous to Central Asia and the Indian Subcontinent. *Cannabis* has long been used for hemp fiber, for oils, for medicinal purposes and as a recreational drug. The *Cannabis* plants produce a group of chemicals called cannabinoids having many beneficial properties (See FIGS. 5A-5E). The majority of these compounds are secreted by glandular trichromes that occur abundantly on the floral calyxes and bracts of female *cannabis* plants.

*Cannabis* legalization in many jurisdictions in the United States has led to strong demand for products that include cannabinoids and terpenes extracted from the *cannabis* plant. When used by humans medicinally, therapeutically or recreationally, *cannabis* can be used by a variety of routes, including vaporizing or smoking dried flower buds and leaf portions, resins, extracted oils, waxes or by transdermal absorption. Likewise, demand has grown in the areas of Pharmaceuticals commonly referred to as "medical marijuana," and in nutritional supplements, edible products, beverages, vaporizer fluids, oils, and transdermal products to just name a few.

Two specific cannabinoids that show tremendous medicinal potential are tetrahydrocannabinol (THC) and cannabidiol (CBD). THC is the decarboxylated cannabinoid that is considered to be psychoactive. However, if the *cannabis* material is never heated, 'decarboxylated', the cannabinoid will remain in its acid form, tetrahydrocannabinolic acid (THCa). THCa is not considered to be psychoactive. THCa also provides many potential medicinal benefits without causing psychoactive effects for the user. Most notably, THCa has many anti-inflammatory and cancer cell fighting properties while not being psychoactive. The cannabinoid CBD also is present in the acid form, cannabidiolic acid (CBDa), if the raw *cannabis* material is not decarboxylated. But when decarboxylated, the CBDa is converted to CBD. Both CBDa and CBD have a different set of potential medicinal properties. For instance, when used alone, CBD is largely best for inflammatory pain, such as that caused by arthritis or injuries

*Cannabis Sativa* has a higher level of THC compared to CBD, while *Cannabis* Indica has a higher level of CBD compared to THC. It has been postulated that *Cannabis* strains with relatively high CBD:THC ratios are less likely to induce anxiety than relatively high ratios of THC:CBD. This may be due to CBD's antagonistic effects at the cannabinoid receptors, compared to THC's partial agonist effect. This likely means the high concentrations of CBD found in *Cannabis* Indica mitigate the anxiogenic effect of THC significantly. The effects of *Sativa* are well known for its cerebral high, hence it is often used during the day as medical *Cannabis*, while Indica is well known for its sedative effects and thus preferred at night for medical *Cannabis* purposes.

The cannabinoid compounds are concentrated in a viscous resin produced in structures known as glandular trichomes of the *Cannabis* plant. More than 85 different cannabinoids have been isolated from the *Cannabis* plant, and some of the more studied cannabinoids include THC, CBD, and cannabinol (CBN). THC is the primary psychoactive component of the *Cannabis* plant.

Cannabinoids found in their natural state typically are in a non-decarboxylated form. Cannabinoids can be converted into a decarboxylated form by a process referred to as decarboxylation. Decarboxylation is a chemical reaction that removes the carboxyl group from a compound. In the case of cannabinoids, decarboxylation involves removing the carboxyl group from the cannabinoid compounds.

A common technique to perform decarboxylation is by heating *cannabis* material to 240° F. or higher for ten minutes to a few hours. Decarboxylation also occurs in *cannabis* material if the material is allowed to be dry cured. These cannabinoids advantageously provide different potential medicinal benefits when they are in their 'raw' or non-decarboxylated form, compared to their properties after they are decarboxylated.

Many of these cannabinoids have also been found to have diverse medicinal uses as shown in FIGS. 5A-5E. For example, CBD can help induce feelings of sleepiness; for this reason, it can be an effective soporific for people who struggle to fall and/or remain asleep due to insomnia and other sleep disorders. Also, CBD is completely non-psychoactive and non-hallucinogenic, meaning that it is physically impossible for it to get you high.

The high from *cannabis* is caused by THC. THC binds tightly to the CB1 and CB2 nerve receptors in the brain and throughout the body. CBD does not bind to these receptors and instead causes its therapeutic actions through more indirect means. In fact, CBD can negate the effects of THC.

While THC has been known to cause anxiety, paranoia, and increased levels of stress along with a high, CBD actually brings about the opposite. For this reason, CBD is being used more and more to treat anxiety and depression.

THC can provide pain relief and is also useful in reducing nausea. Research shows THC has sedative effects and can make it easier to fall asleep. There's also emerging evidence suggesting that THC may improve breathing during sleep, which makes THC a potential therapy in the treatment of certain breathing disorders. THC can also be helpful to people who have conditions such as Post Traumatic Stress Disorder (PTSD) that involve frequent, disturbing dreams and nightmares. People may experience fewer dreams when using *cannabis* regularly because it may help to decrease the amount of REM (Rapid Eye Movement) sleep a person gets. REM sleep, the final stage in the sleep cycle, is when almost all dreaming occurs (See FIGS. 5A-5E).

Cannabinol, or CBN, is a less well-known cannabinoid than CBD and it is formed when THC is heated for too long or at too high of a temperature. It appears to have powerful sedative effects, which may be enhanced when its combined with THC. CBN also has pain-relieving, anti-inflammatory properties. CBN is formed when THC is heated for too long or at too high of a temperature. According to pioneering *cannabis* lab Steep Hill: Of all the cannabinoids, CBN appears to be the most sedative. Not only is it sedative, it takes very little to do the job. The consumption of 2.5 mg to 5 mg of CBN has the same level of sedation as a mild pharmaceutical sedative, with a relaxed body sensation similar to 5 mg to 10 mg of diazepam. CBN is synergistic with both CBD and D9THC for inducement of sleeping, and when mixed in the correct ratios, CBN becomes an effective sleep aid of 5-6 hours duration (See FIGS. 5A-5E).

b. Terpenes

Terpenes are tiny, aromatic molecules produced in a variety of plants such as the *cannabis* plant. They are the product of essential oils in plants and flowers that create smell and taste. They also appear to play a pretty significant role in the effects of *cannabis*, including its ability to affect sleep (See FIGS. 6A-6F).

Myrcene is a terpene found in *cannabis*, and it is also found in a lot of fruits and herbs, including mangoes, basil, thyme, and lemongrass, as well as in the sleep-promoting plants hops and ylang ylang. Myrcene has been shown to have sedative effects and it also functions as an anti-inflammatory. Moreover, acting as a regulator, myrcene can enhance or diminish the effects of other terpenes and cannabinoids (See also FIGS. 6A-6F).

Caryophyllene is a stress, anxiety and pain-relieving terpene that may also promote sleep, thanks to these relaxing, anxiolytic and analgesic properties (See also FIGS. 6A-6F). This terpene has a peppery, spicy scent, and is also found in cloves and black pepper.

Limonene is a citrus-flavored terpene, which is found in citrus peels as well as in *cannabis* and other plants, has been shown to reduce anxiety and stress, according to research. Limonene may also have anti-depressant effects. And research shows it may reduce OCD behaviors. Scientists think its calming, mood-lifting effects come from limonene's ability to elevate serotonin levels in the brain. That may also make this terpene a sleep-promoter (See also FIGS. 6A-6F).

Linalool is a lavender-scented terpene found in hundreds of plants, including *cannabis*. Linalool is also found in lavender, mint, cinnamon and coriander. This terpene has very strong sedative and relaxing properties. In fact, studies show linalool lowers anxiety and depression symptoms, as well as help guard the immune system against damage from stress. Linalool also increases adenosine, a sedating hormone that helps us fall asleep. Patients suffering from arthritis, depression, seizures, insomnia and even cancer, have all found aid in this amazing terpene (See also FIGS. 6A-6F).

Terpenes and cannabinoids work better together. For example, when looking for specific *cannabis* effects or treatments, it's important to remember that terpenes and cannabinoids in *cannabis* work together to synergistically increase the potency of the plant. This is what many refer to as the entourage effect, which explains why whole-plant *cannabis* tends to provide more potential medicinal benefits than isolated cannabinoids.

c. Transdermal Delivery and Topical Application

Substances such as cannabinoids and/or terpenes can enter the body through various means. Drugs can be smoked, snorted, inhaled, injected, swallowed as pills, or applied through transdermal means (applied to the skin and/or topical application) Some substances can be eaten or drank, such as marijuana and alcohol. Regardless of how a substance enters the body, it is carried through the bloodstream to various organs, including the brain. The method by which a drug is administered, along with other factors, determines the speed of onset of effects. Drugs undergo four stages within the body: absorption, distribution, metabolism, and excretion. After a drug is administered, it is absorbed into the bloodstream. The circulatory system then distributes the drug throughout the body. After the drug has had its effect, it is then metabolized by the body. The drug is then excreted, primarily through urine or feces.

Although comparable to oral dosage forms in term of efficacy, transdermal delivery of substances provides numerous advantages. Transdermal administration avoids the first pass metabolism effect (e.g., by liver) that is associated with the oral route and thus improves drug bioavailability. Furthermore, transdermal administration allows a steady infusion of a drug to be delivered over a prolonged period of time, while also minimizing the adverse effects of higher drug peak concentrations, which can improve patient adherence. Enhancers may also be also added to transdermal formulations to increase the penetration of permeants by disrupting the structure of the skin's outer layer, increasing penetrant solubility.

In this disclosure, medication and sedative substance refers to the promotion of health, wellness, healing and well-being via an external sleep-aid device having transdermal delivery features. Importantly, in this disclosure, these statements are not intended to represent that the present invention is configured diagnose, treat, or cure any disease.

DETAILED DESCRIPTION

It should be understood that the foregoing relates to various embodiments of the present invention which can be carried out independently and/or in combination and that modifications may be made without departing from the spirit and scope of the invention. It should be further understood that the present invention is not limited to the designs mentioned in this application and the equivalent designs in this description, but it is also intended to cover other equivalents now known to those skilled in the art, or those equivalents which may become known to those skilled in the art in the future.

In various embodiments, therapy tapes comprise handles (e.g., detachable and/or secured relative to a backing layer) and/or stimulators (e.g., vibrators, pressure applicators, transcutaneous electrical nerve stimulation devices (TENS devices), and/or the like) to facilitate therapeutic treatment of a patient injury, disability, medical treatment site, and/or the like. The therapy tape may comprise a backing material configured to support additional features of the tape, an adhesive layer configured to selectably secure the tape against a surface of a flexible material (e.g., a patient's skin), one or more handles, and/or one or more stimulators. The handles may be integrated into the tape to enable a healthcare professional (e.g., physician, physical therapist, and/or the like), the patient, and/or another individual to manipulate the material (e.g., skin). For example, the handles may enable the healthcare professional and/or the patient to pull, stretch, twist, extend, elongate, and/or the like the underlying skin, tissue, fascia, and/or the like as a part of a medical treatment (e.g., a medical treatment including stretching, pulling, pushing, twisting, and/or the like the underlying skin, tissue and/or fascia of a patient) to encourage blood flow within and/or proximate the skin to which the tape is secured, to break-up and/or discourage scar tissue development, to encourage muscle development, to improve lymphatic flow and/or drainage, to increase fluid flow within a patient's body, to increase metabolic rate of a patient's body, and/or the like. Hence, the adhesive layer of the tape may be configured to be securely fastened against the patient's skin such that pulling and/or manipulating one or more handles of the tape does not cause the tape to detach from the patient's skin. Moreover, the therapy tape may be configured to vary in length and/or width, for example, as it is stretched, compressed, and/or the like.

In various embodiments, the therapy tape comprises one or more stimulators configured to stimulate the patient's skin while the tape is secured to the patient. In various embodiments, the therapy tape may comprise an integrated controller comprising a power supply and/or one or more control devices configured to selectably activate and/or deactivate the one or more stimulators. In various embodiments, the controller may be configured for wireless and/or wired connection with an external computing device (e.g., handheld computing device, desktop computing device, laptop computing device, control panel, and/or the like). The controller may be configured to transmit signals to the computing device indicative of current and/or historical status of the one or more stimulators, and/or may be configured to receive one or more control signals from the external computing entity configured to manipulate operation of the one or more stimulators.

In various embodiments, therapy tape may comprise a plurality of stimulators (e.g., a plurality of stimulators of the same type and/or a variety of types of stimulators) and/or one or more handles. Accordingly, the therapy tape may be configured to provide a variety of therapy types for the patient.

In various embodiments, the therapy tape may be configured to remain secured against a patient for an extended period of time (e.g., one hour or greater than one day). In such embodiments, the therapy tape may be configured to enable a patient to self-provide therapy when not in direct communication with a healthcare professional.

In various embodiments, the therapy tape may be configured to be stored on a roll, and a length of tape may be removed and detached (e.g., cut) from the roll for use Backing Layer and Transdermal Delivery Features, Including Topical Application In various embodiments, a therapy tape may comprise a backing layer having an adhesive layer secured thereto. In certain embodiments, the backing layer may additionally have one or more handles and/or one or more stimulators secured thereto.

The backing layer may comprise a woven or nonwoven material, such as a woven fabric, a nonwoven film, a nonwoven fabric, and/or the like. In various embodiments, the backing layer may comprise a single layer, however in certain embodiments, the backing layer may comprise a plurality of layers (e.g., a woven layer and a non-woven layer). In certain embodiments, the backing layer may comprise a plurality of fibers (e.g., woven fibers, blown fibers, and/or the like). The plurality of fibers may comprise reinforcing fibers having a high tensile strength and configured to impede undesirable tearing and/or breaking of the tape. Moreover, in certain embodiments, the plurality of fibers may comprise elastic fibers configured to enable the backing layer to reversibly stretch in one or more directions.

In various embodiments, the backing layer may comprise one or more natural and/or synthetic materials. For example, the backing layer may comprise plant-based materials (e.g., cotton, wood fibers, bamboo fibers, cellulose fibers, natural rubber, and/or other biodegradable materials) synthetic materials, (e.g., polyester, synthetic rubber, polyvinyl chloride, and/or the like), and/or the like. In various embodiments, the backing layer may be hydrophobic, such that the backing layer may dry quickly when exposed to a moist environment (e.g., sweat, water, and/or the like). However, in certain embodiments, at least a portion of the backing material may be hydrophilic. As specific examples, the backing layer may comprise a Kinesiology tape backing layer, a therapeutic support tape backing layer, an athletic tape backing layer, a dynamic tape backing layer, and/or the like. In various embodiments, the backing layer may comprise a plurality of materials. For example, a first portion of a backing layer may comprise a first material and a second portion of the backing layer may comprise a second material. As a specific example, a first portion of the backing layer may comprise a flexible, inelastic material and a second portion of the backing layer may comprise a flexible, elastic material.

In various embodiments, the backing layer may be a porous material, having a plurality of pores extending therethrough between a top surface and a bottom surface. For example, the pores may extend between fibers of a woven material, and/or through openings within a nonwoven material. Accordingly, the backing layer may be breathable, thereby allowing gases (e.g., air) to flow through the backing layer. Accordingly, the backing layer may enable air to flow to and/or away from a patient's skin located adjacent the therapy tape when secured thereto.

In various embodiments, the backing layer may be stretchable and/or elastic in one or more directions. For example, the backing layer may be stretchable and/or elastic in a direction parallel to the length of the tape and/or in a direction parallel to the width of the tape. Accordingly, in certain embodiments, the backing may be configured to provide a tensile force to a patient's skin when the therapy tape is secured thereto. For example, the elastic backing layer (and accordingly the remainder of the therapy tape) may be stretched during application to a patient and released once applied. Accordingly, the therapy tape may thus apply a tensile force as a result of the stretched elastic backing layer attempting to return to its original, unstretched form. However, it should be understood that in certain embodiments, the backing layer may be inelastic and may resist stretching (e.g., elongating).

Another aspect of the present invention is to provide a soft tissue mobilizing device having an attachable, back surface having transdermal delivery features suitably configured to deliver an active ingredient (i.e., therapeutic or dietary supplement) of at least one cannabinoid, anti-inflammatory substance, terpene and/or a CBD derived from fruit, plants, vegetables, tree bark and/or a combination thereof through the skin and/or the myofascial and/or musculoskeletal tissue area of a user/mammal in order to help alleviate pain and to speed up the healing process.

In various embodiments, a substance such a lotion, cream, gel and/or oil having a chemical composition and/or an active ingredient of cannabinoid and/or terpene can be applied directly to a user's skin prior to applying the soft tissue device directly to the soft tissue area of a user's body. The applied device will help to decompress the soft tissue area being treated and the substance applied to the user's skin will help to extend the widespread potential therapeutic benefits of cannabinoids and/or terpenes.

The back surface of the present invention includes an adhesive for allowing the device to be applied directly to a soft tissue area of a user's body where muscle tension, inflammation, aches and pain are present. The applied device will also help to decompress the soft tissue area being treated and the back surface can include transdermal delivery features.

A further aspect of the present invention is to advantageously provide a method for treating myofascial and/or musculoskeletal imbalances by applying a beneficial transdermal soft tissue mobilizing device directly to a soft tissue area where a user is experiencing myofascial and/or musculoskeletal tissue imbalances.

Adhesive Layer

As discussed herein, the therapy tape may comprise an adhesive layer secured to the backing layer. The adhesive layer may be configured to selectably secure the therapy tape against a patient's skin. Accordingly, the adhesive layer may be secured against the backing layer such that the adhesive layer and backing layer do not delaminate during application and/or removal from the patient.

In various embodiments, the adhesive layer may be secured against the backing layer via any of a variety of processes, as discussed in greater detail herein. For example, the adhesive layer may comprise an adhesive sheet laminated against the backing layer, an adhesive spray sprayed onto the backing layer, an adhesive liquid rolled onto the backing layer, dripped onto the backing layer, and/or the like. The adhesive layer may also be comprised of an adhesive suitably mixed with a substance such as at least one cannabinoid and/or terpene for transdermal delivery. In various, an effective amount of a skin permeation enhancer is placed on the back surface of the device or the pad or on the user's skin. The skin permeation enhancer has an HLB of about 6-30.

In various embodiments, the adhesive layer may be continuous, such that at least substantially an entire surface of the backing layer is covered with the adhesive layer. However, in certain embodiments, the adhesive layer may be discontinuous, and may thus comprise a plurality of spaced adhesive portions secured to a surface of the backing layer. For example, the adhesive layer may comprise a plurality of spaced rectangular, circular, triangular, and/or the like adhesive portions therein. In various embodiments, the adhesive layer may be breathable (e.g., through adhesive portions and/or between adhesive portions) such that gases (e.g., air) may flow through the backing layer and the adhesive layer.

Like the backing layer, the adhesive layer may be elastic and/or stretchable, such that the elastic layer may move and/or stretch with the backing layer. Accordingly, the adhesive layer may be configured to conform with the movement of the backing layer such that the adhesive layer does not provide any force relative to the backing layer that may cause the adhesive layer to delaminate from the backing layer.

In various embodiments, the adhesive layer may be configured to detachably secure the therapy tape against a patient's skin. In various embodiments, the adhesive layer may provide sufficient tensile strength between the therapy tape and the patient's skin that manipulating the therapy tape (e.g., via handles) may cause relative manipulation of the patient's skin, and the therapy tape may remain secured to the patient's skin. In various embodiments, the adhesive layer may have a low shear strength to facilitate removal of the therapy tape from the patient, such as by stretching the therapy tape relative to the patient's skin.

In certain embodiments, the adhesive layer may be heat-activated to enable the therapy tape to be secured to a patient's skin and/or to be removed from the patient's skin and/or active transdermal delivery features such a therapeutic substance (e.g., cannabinoid). Accordingly, the therapy tape may be secured to a patient's skin, and the patient's body heat may sufficiently heat the therapy tape to activate the adhesive layer and/or substance such that the tape is secured relative to the patient's skin. Once activated and secured to the patient's skin, the therapy tape may be manipulated together with the patient's skin (e.g., via handles) without the therapy tape become dislodged from the patient's skin.

Handle

With reference to the figures, the therapy tape may comprise one or more handles secured relative to the backing layer to enable lifting of the therapy tape and the underlying flexible material (e.g., skin) to which it is secured. The therapy tape may have a single handle and/or a plurality of handles having any of a variety of configurations. In some embodiments, the handles are attachable and detachable. In other embodiments, the handles are pivotable. In various embodiments as discussed herein, the handles may be hook-shaped, circular, "U"-shaped, "D"-shaped, and/or the like. For example, in various embodiments handles may be O-rings, U-rings, J-rings, D-rings, and/or the like. In various embodiments, the handles of the therapy tape may be secured relative to the backing layer such that the handle concentrates tensile forces applied to the handle along a center portion of the backing layer in order to impede peeling of the tape from the applied patient's skin.

Methods Systems

A method of the present invention includes the steps of: decompressing the soft tissue area being treated with the applied device having transdermal beneficial features; manually lifting and shifting the device, where the manual lifting and shifting enhances relief of myofascial and/or musculoskeletal tissue imbalances; normalizing the myofascial and/or musculoskeletal tissue area being treated by manually lifting and shifting the soft tissue, wherein the normalizing time period is reduced; and delivering an active ingredient of at least one cannabinoid, terpene and/or a CBD derived from fruit, plants, vegetables, tree bark and/or a combination thereof to treat the imbalanced soft tissue area of the user to help alleviate pain, reduce inflammation and to speed up the healing process in mammals.

An additional aspect of the invention is to provide a system for treating myofascial and/or musculoskeletal imbalances that is comprised of a novel soft tissue mobilizing device having a front surface and a back surface having transdermal delivery features.

In one embodiment, the system includes a transdermal soft tissue mobilizing device for: applying directly to a selected soft tissue area where a user is experiencing myofascial and musculoskeletal tissue imbalances; decompressing the soft tissue area being treated; manually lifting and shifting the soft tissue area, wherein the manual lifting and shifting enhances relief of myofascial and musculoskeletal tissue imbalances; normalizing the myofascial and musculoskeletal tissue area treated by manually lifting and shifting the soft tissue, the normalizing time period is reduced; and delivering an active ingredient of at least one cannabinoid, terpene and/or a CBD derived from fruit, plants, vegetables, tree bark and/or a combination thereof to treat the imbalanced soft tissue area of the user to help alleviate pain, reduce inflammation and to speed up the healing process.

In a further embodiment, a substance such a lotion, cream, gel and/or oil having chemical composition and an active ingredient of cannabinoid and/or terpene can be applied directly to a user's skin prior to applying the soft tissue device directly to the soft tissue area of a user's body.

Another aspect of the present invention is to provide a method of transdermal soft tissue therapy for removing or breaking up fibrous (soft tissue) adhesions by allowing a user to utilize a transdermal soft tissue mobilizing device by manually lifting and shifting via a flossing motion for administering a beneficial constant force to an affected soft tissue area until relief occurs and for delivering an active ingredient of at least one cannabinoid, terpene and/or a CBD derived from fruit, plants, vegetables, tree bark and/or a combination thereof to help alleviate pain, reduce inflammation by the transdermal features of the tape and to speed up the healing process.

In this disclosure, medication refers to the promotion of health, wellness, healing and well-being in a mammal via a mobilizing device having transdermal delivery features. Importantly, in this disclosure, these statements are not intended in any way, shape or form to represent that the present invention is configured diagnose, treat, or cure any disease.

Figure 1B:
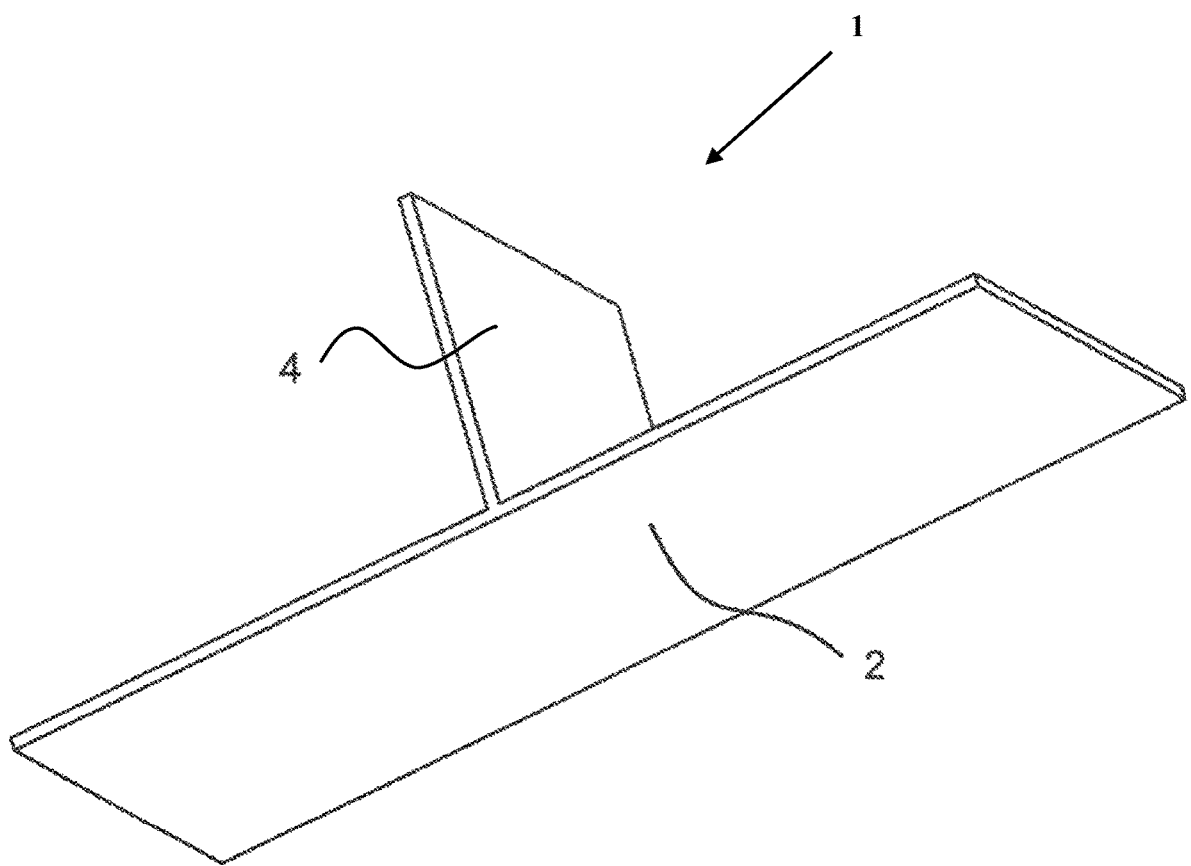
Figure 1C:
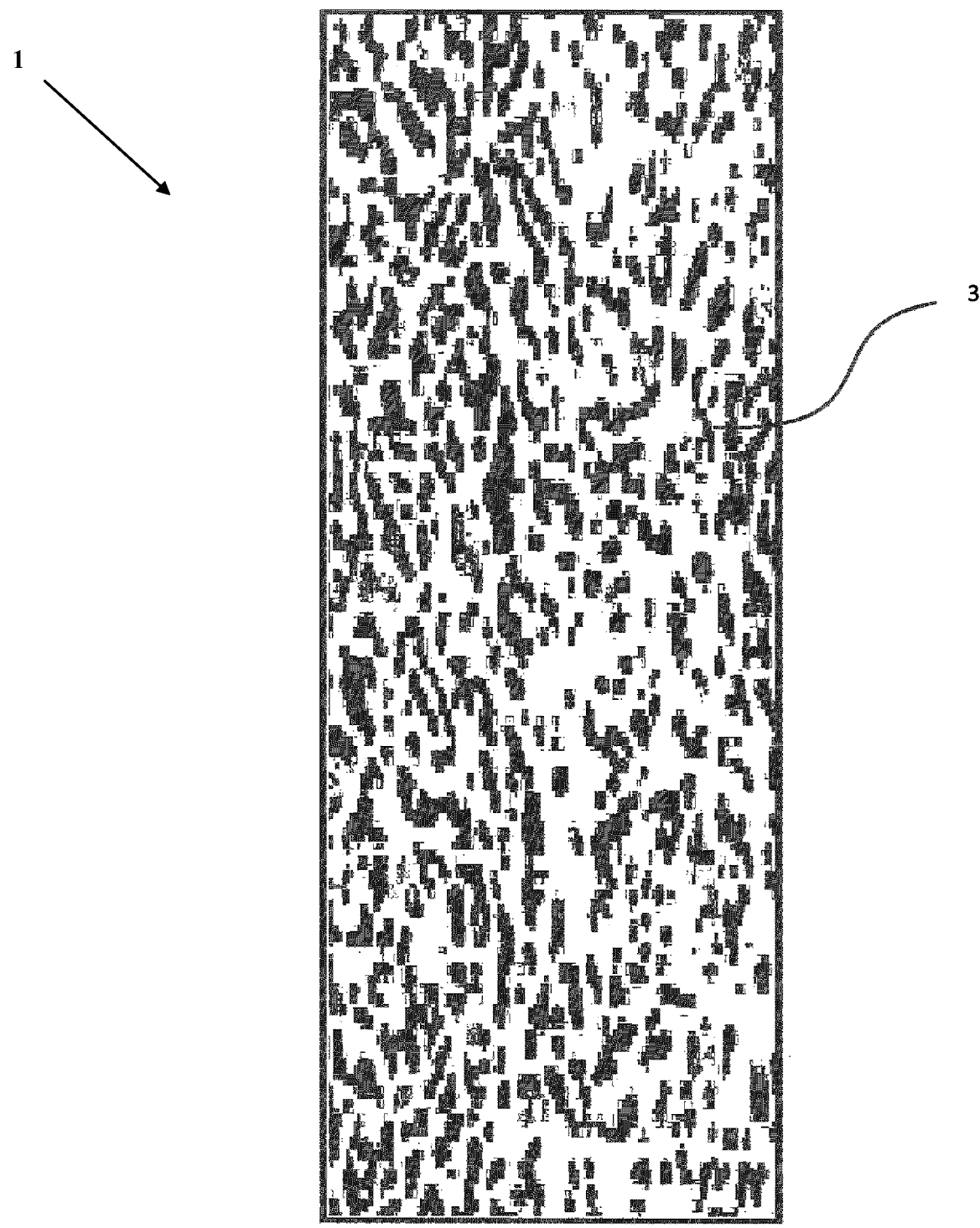

FIGS. 1A-1C refer to therapy tape 1 (also referred to as a soft tissue mobilizing device) used for treating myofascial and/or musculoskeletal tissue imbalances. The device 1 will be comprised of a front surface 20. The front surface 20 will include at least one-tab gripping mechanism 4 (handle) as depicted in FIGS. 1A-1B. The tab gripping mechanism 4 will allow a user such as a patient, a physical therapist, a physician, horse therapist/trainer and/or the like to grip the tab 4 for manually lifting and/or shifting the soft tissue area being treated.

Figure 16A:
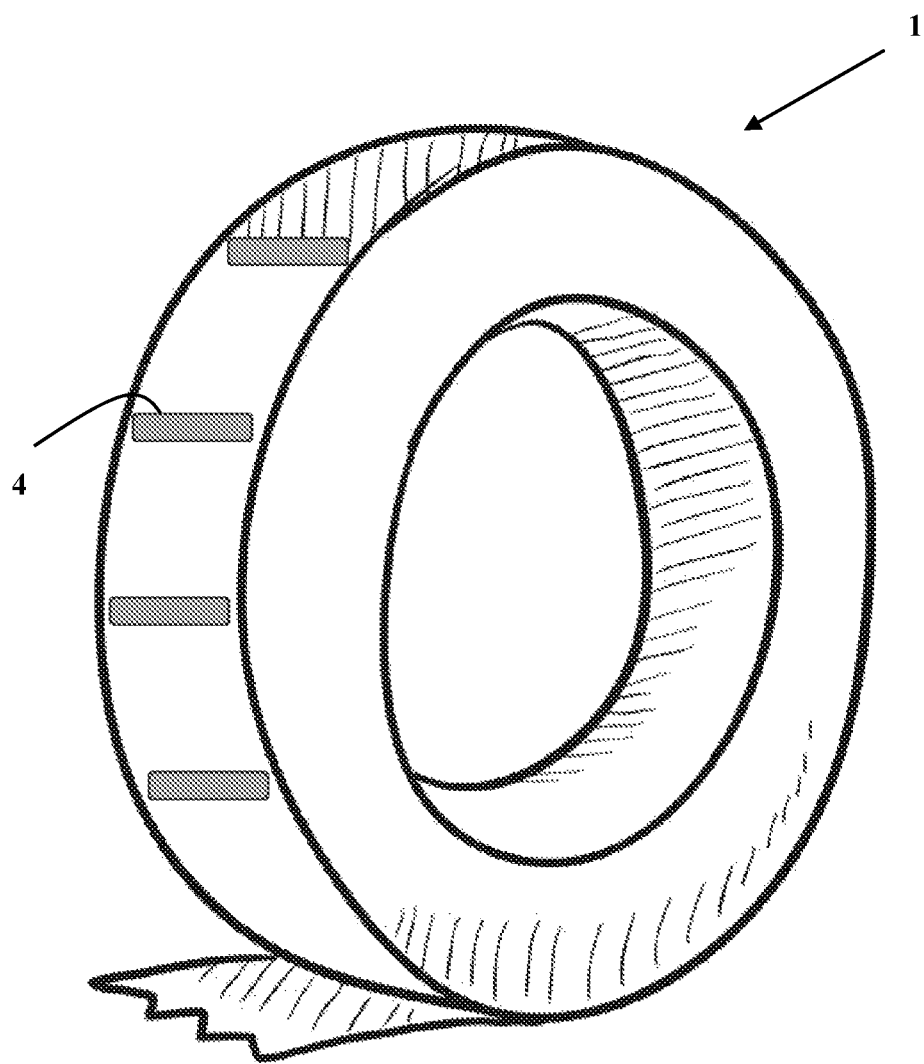
FIGS. 16A-16B show various embodiments of the therapy tape configured in a roll for use.
Figure 16B:
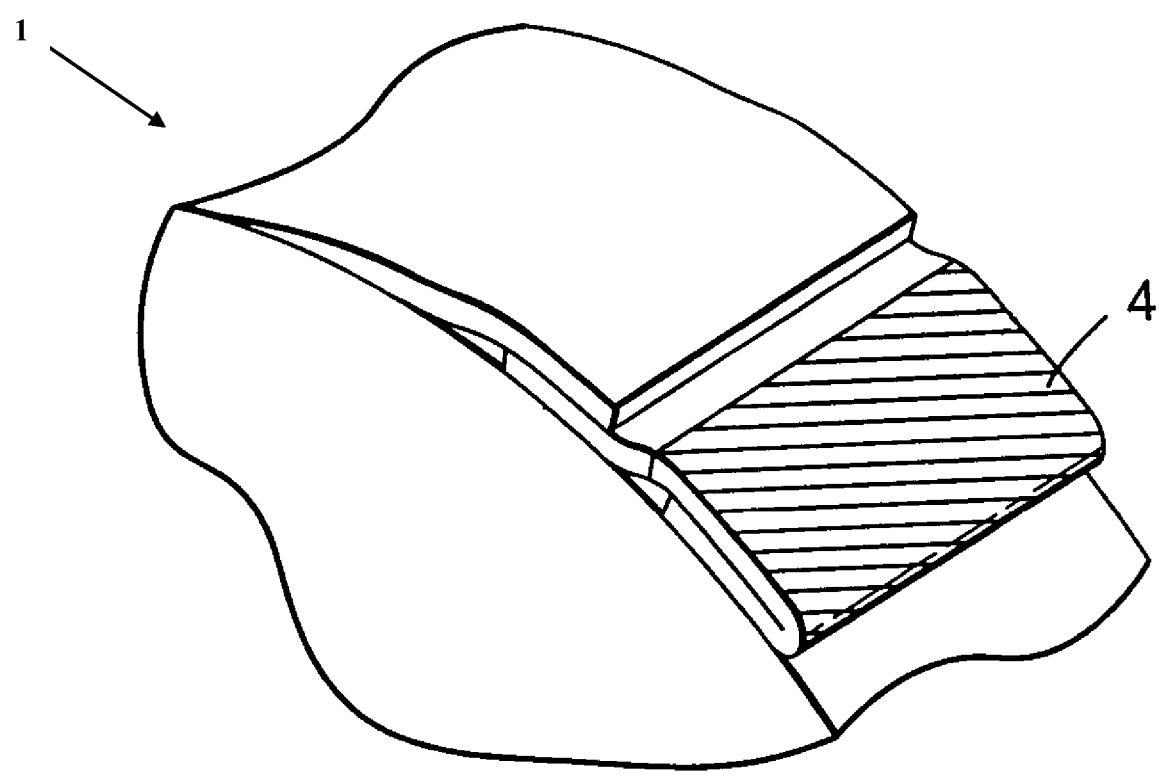
Figure 17A:
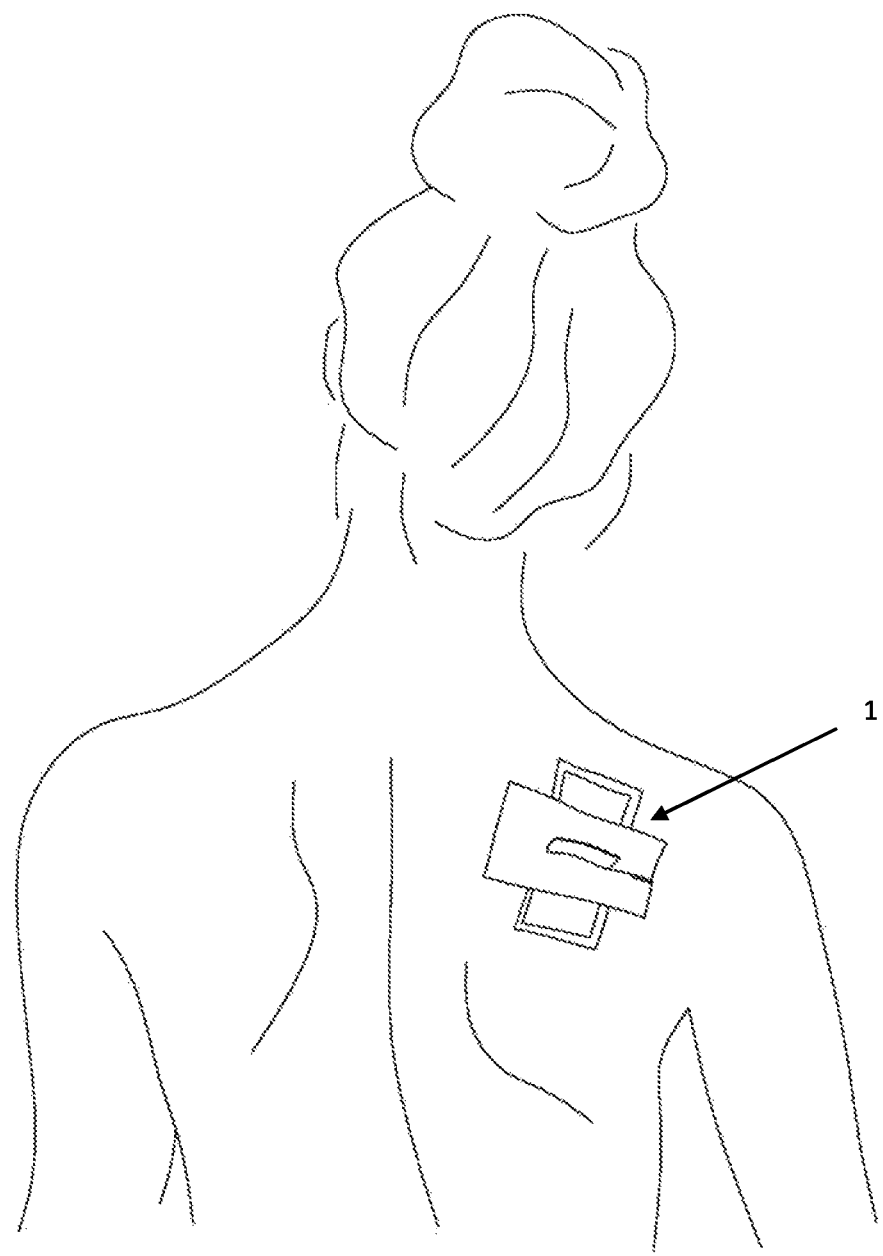
FIGS. 17A-17E show various embodiments of the soft tissue mobilizing device in use.
Figure 17B:
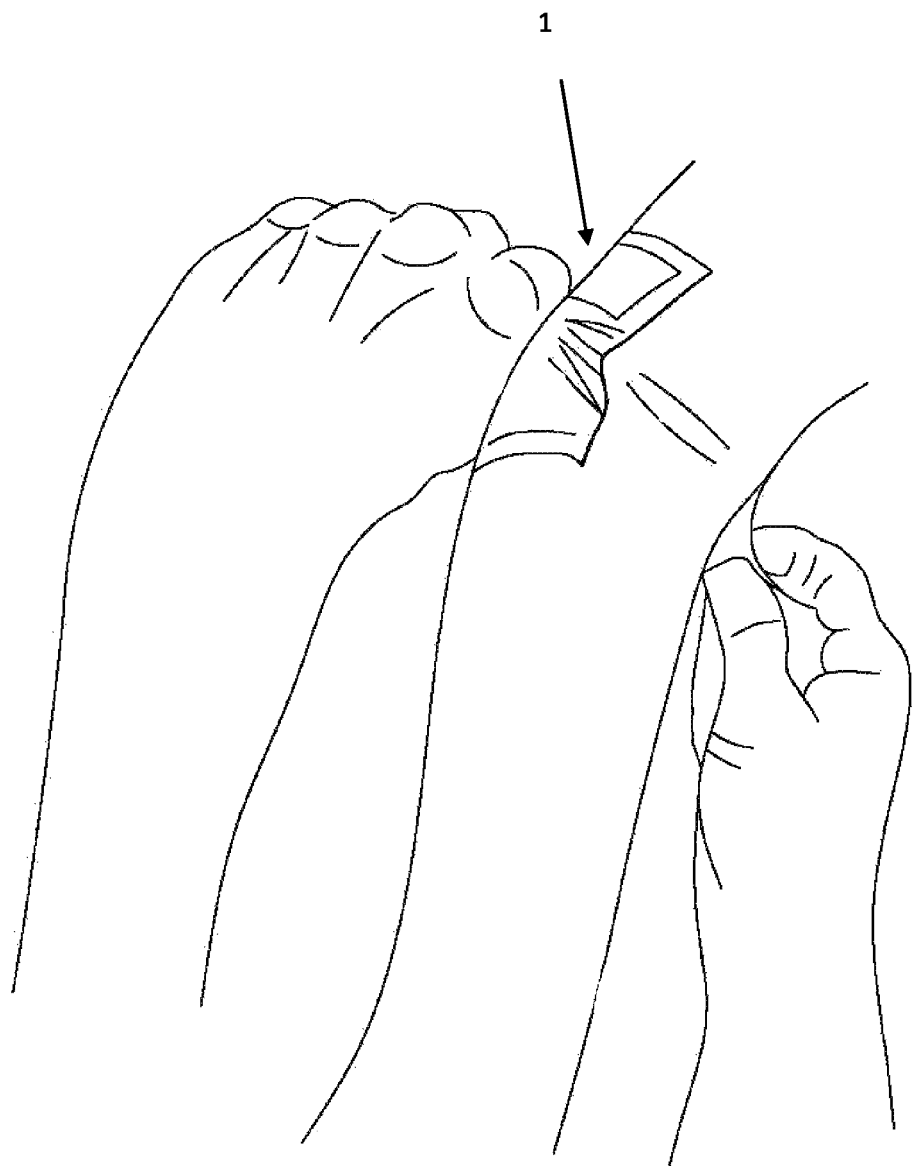
Figure 17C:
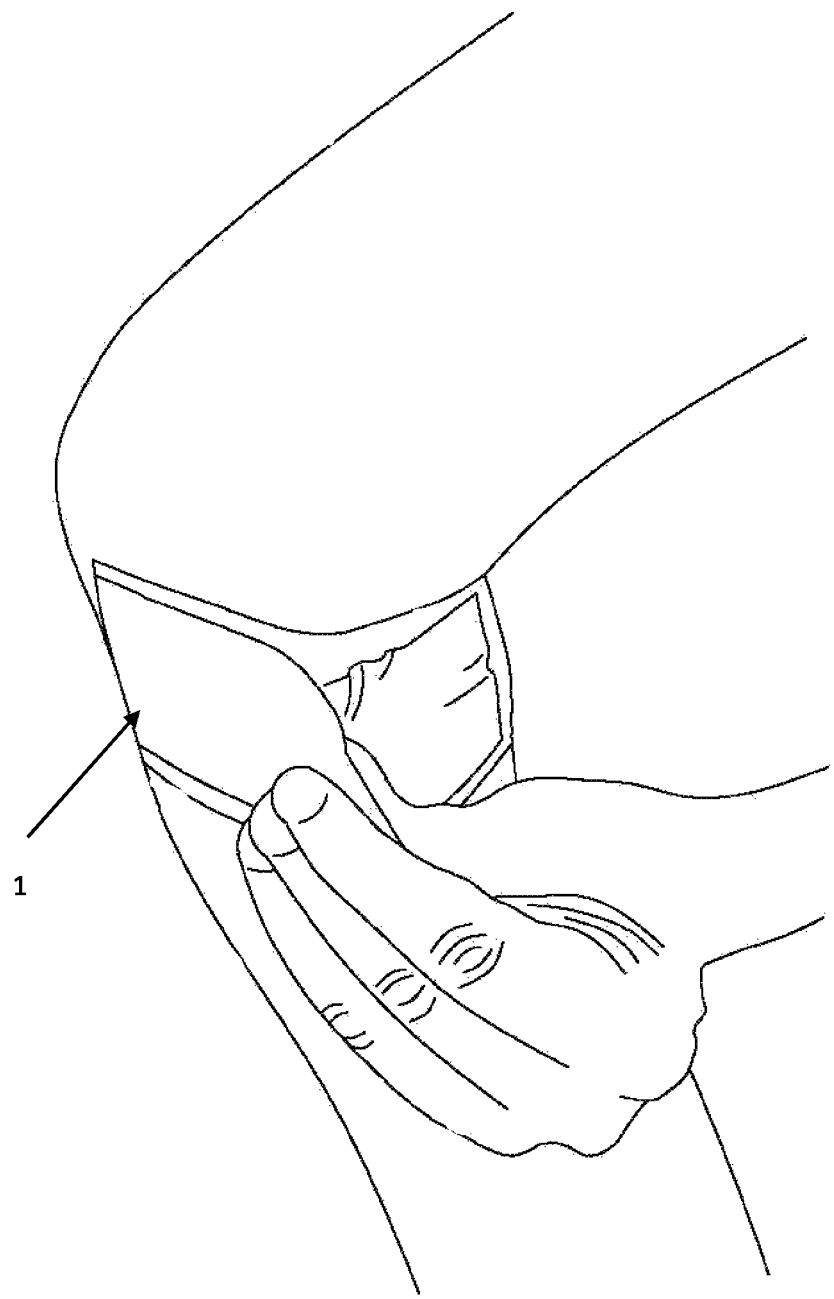
Figure 17D:
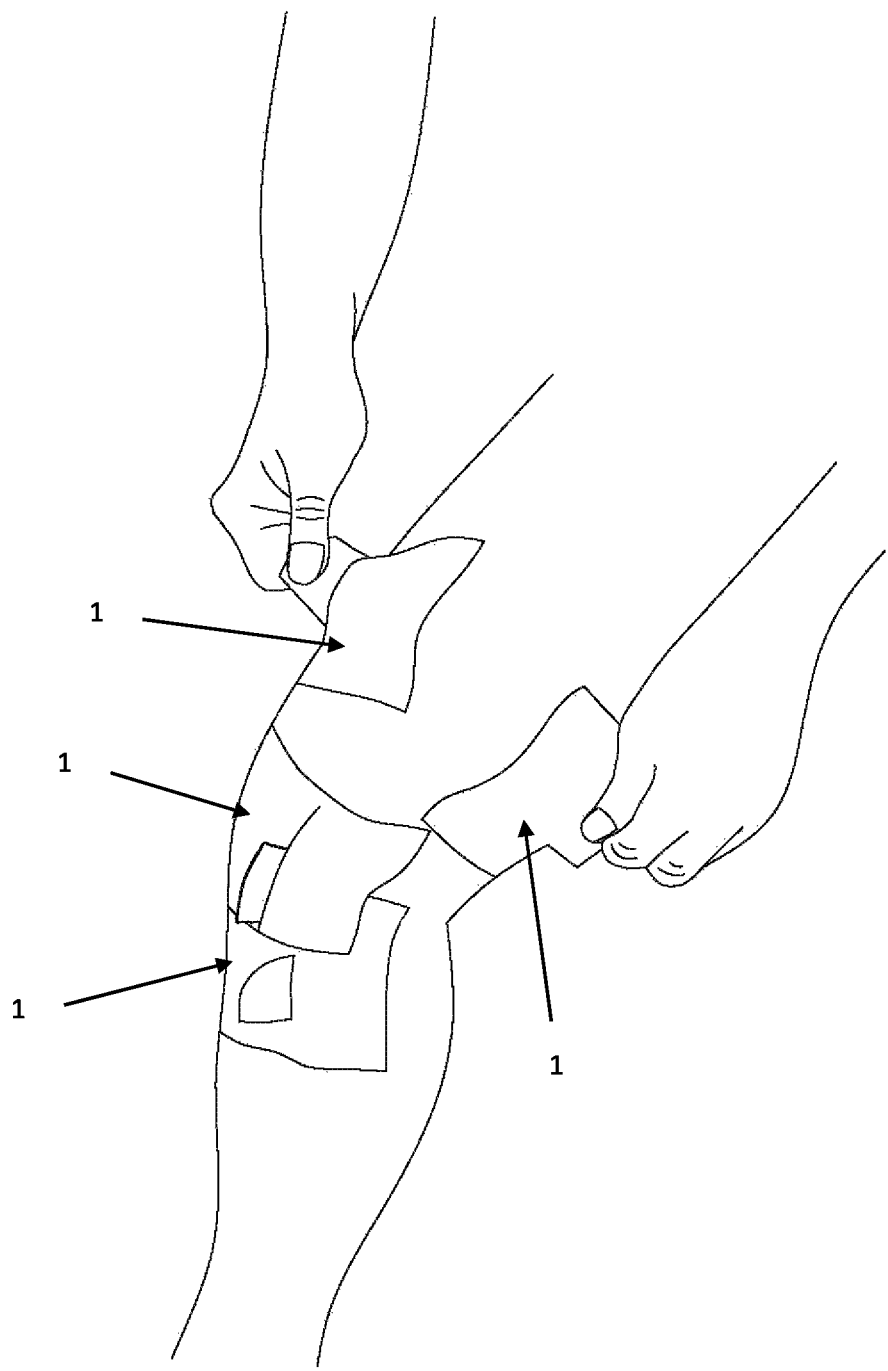
Figure 17E:
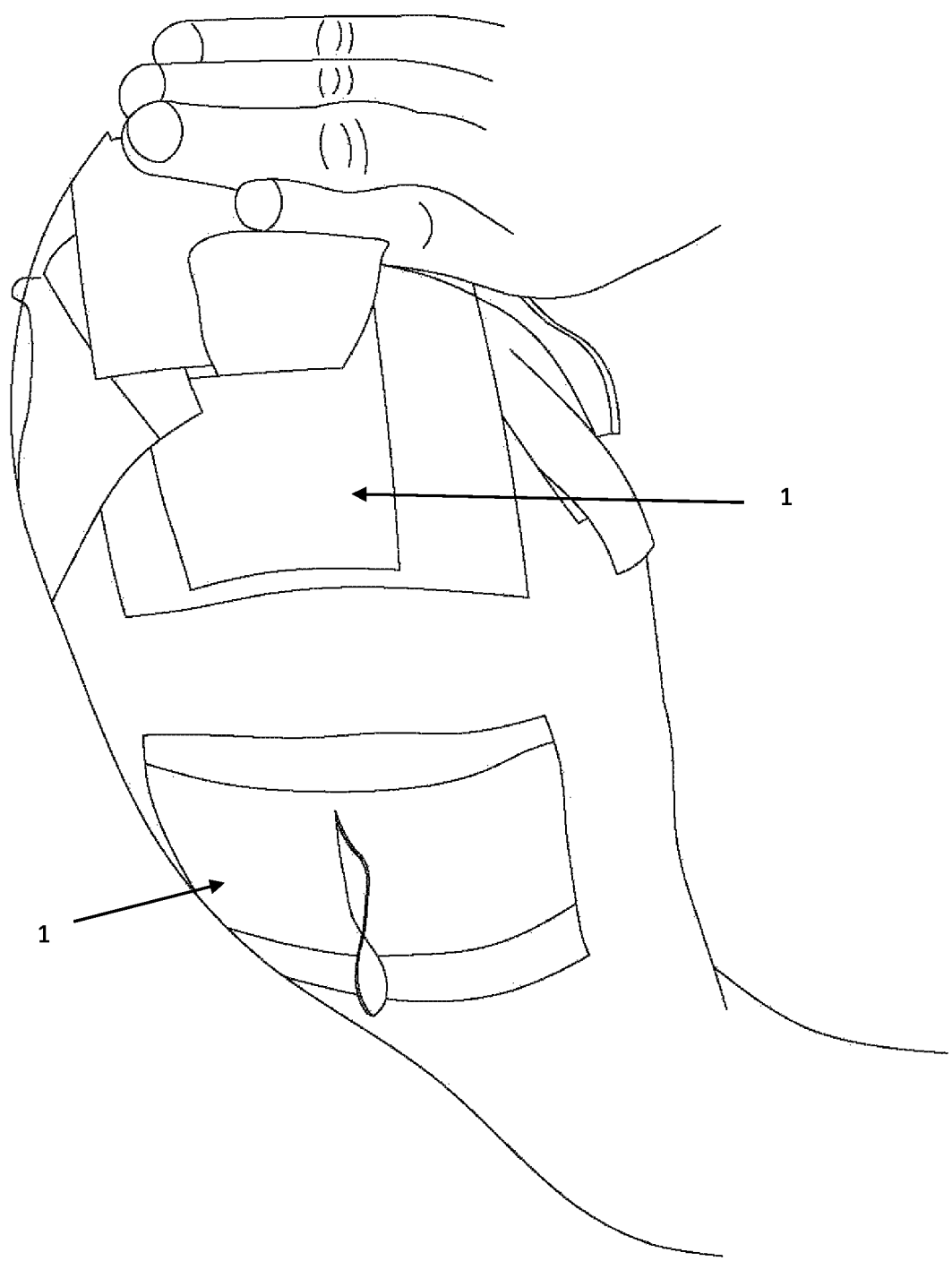

The therapy tape 1 may have a single handle 4 and/or a plurality of handles 4 having any of a variety of configurations. In some embodiments, the handles 4 are attachable and detachable. In other embodiments, the handles 4 are pivotable as shown in FIG. 16.

As shown in FIG. 1B, the therapy tape 1 may comprise a backing layer 2 that can include transdermal features 50 and a handle 4 positioned at least substantially centrally with the therapy tape 1. The handle 4 may be continuous with the backing layer 2 and may be defined by a folded portion of the backing layer 2. In certain embodiments, the handle 4 may comprise a Kinesiology tape material, a medical/therapeutic support tape material, an athletic tape material, a dynamic tape material, and/or the like.

The therapy tape 1 has a back surface/backing layer 2. The backing layer 2 includes an adhesive later 3 as shown in FIG. 1C for allowing the tape 1 to be applied directly to a soft tissue area of the user's body where muscle tension, aches, inflammation, and pain are present. The adhesive located on the back surface 2 also has an adhesive and cohesive strength that will vary depending on the amount of force required to treat a user's myofascial and/or musculoskeletal tissue imbalances. Further, the type of adhesive used on the back surface 2 can vary as well.

People who take anti-inflammatory drugs orally increase their risk of developing severe bleeding in their stomachs. They may also be at risk for heart attacks and strokes. These risks get worse if they take higher doses. It gets even worse if they take these medicines for a long period of time. Other side effects can include feeling bloated, heartburn, nausea, vomiting, diarrhea and/or constipation. The side effects also depend on the specific type of anti-inflammatory drug taken but largely include an increased risk of gastrointestinal ulcers and bleeds, heart attack, and kidney disease. The present invention may eliminate these side effects by providing a therapy tape comprised of transdermal delivery features, whereby a user does not have to use ingestible medicines and/or substances to relieve pain, tissue imbalances and/or reduce inflammation.

In various embodiments, the transdermal substance(s) will be comprised of substances having features to reduce inflammation, wherein a user does not have to use ingestible medicines and/or substances to relieve and/or reduce inflammation. This will also allow a person to possibly avoid stomach irritation from said medicine and/or avoid ulcers, bleeding, or holes in the stomach or intestine. These problems may develop at any time during treatment, which may happen without warning symptoms, and may cause death.

Stimulators and Controller

Figure 2:
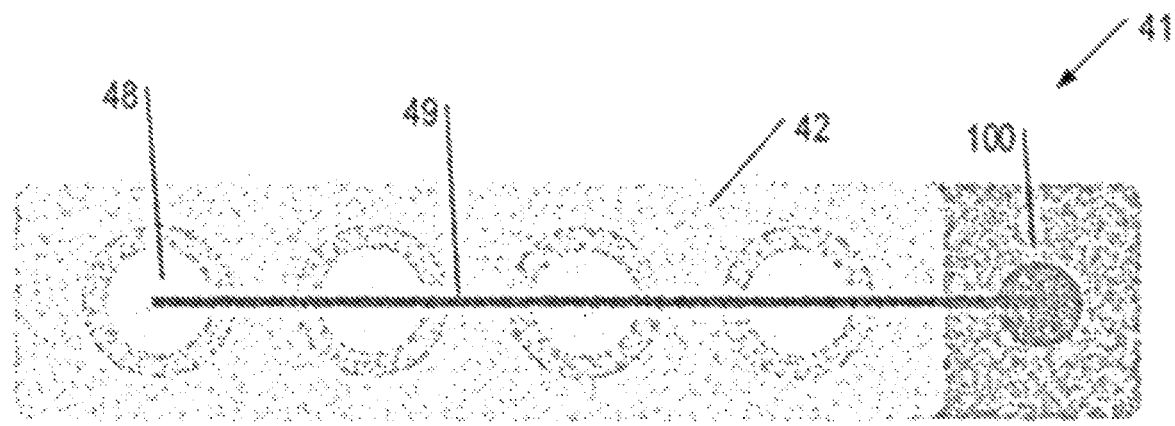
FIG. 2 shows a top view of a therapy tape having various stimulators according to one embodiment.
Figure 3A:
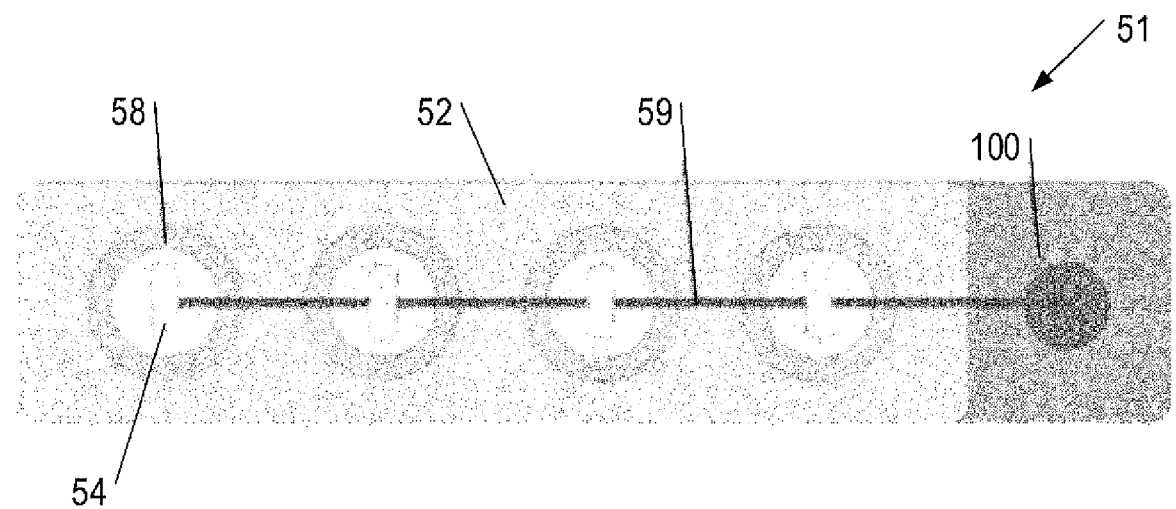
FIGS. 3A-3B show top and side views of a therapy tape comprising stimulators according to one embodiment.
Figure 3B:
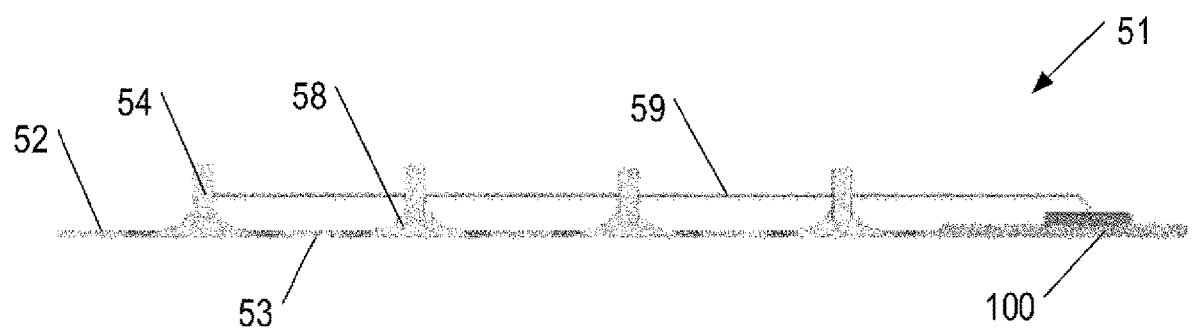
Figure 3C:
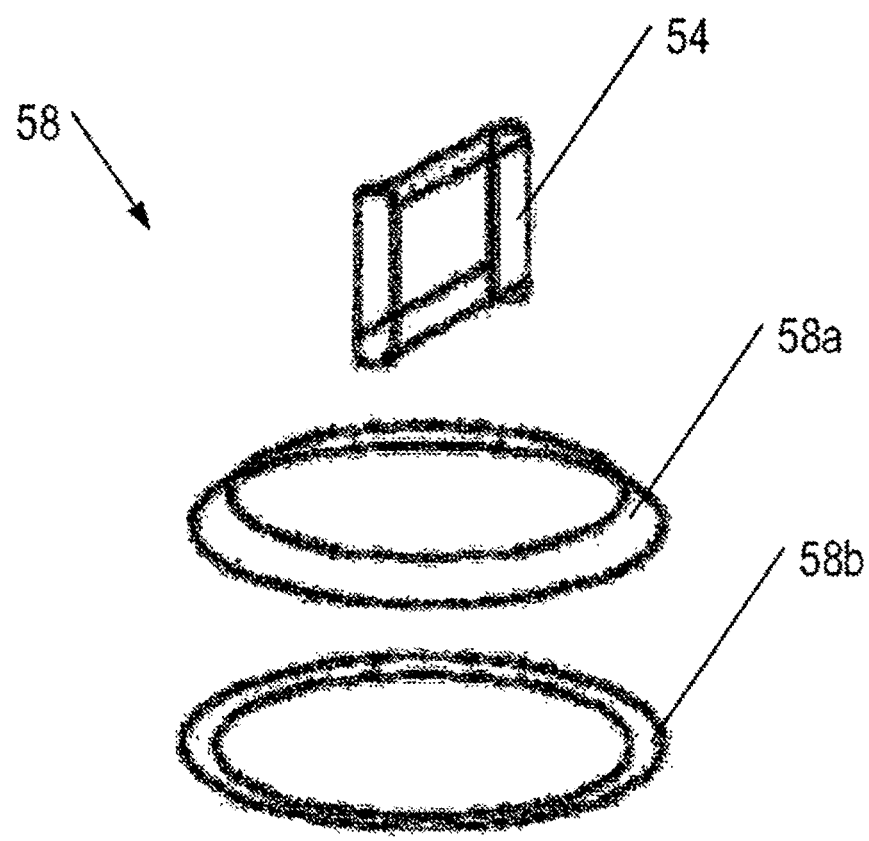
FIG. 3C shows an exploded view of a stimulator and handle according to one embodiment.
Figure 4:
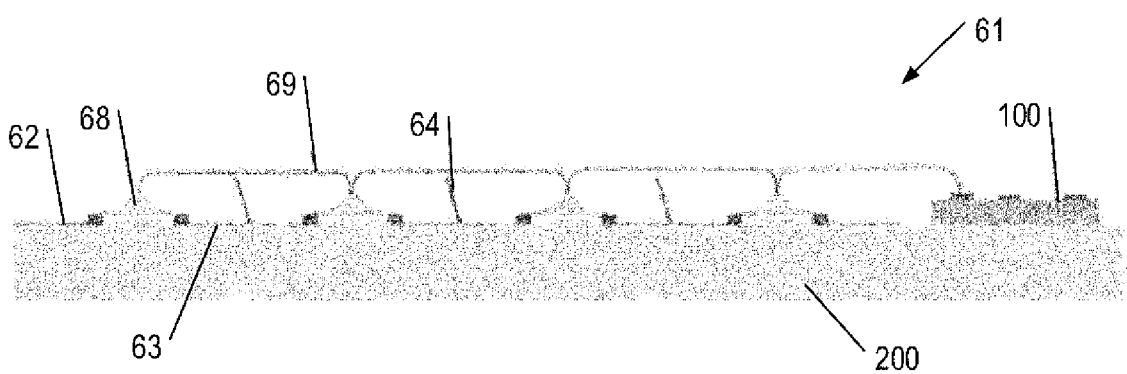
FIG. 4 shows a side view of an example therapy tape comprising stimulators secured against a patient's skin according to one embodiment.
Figure 5A:
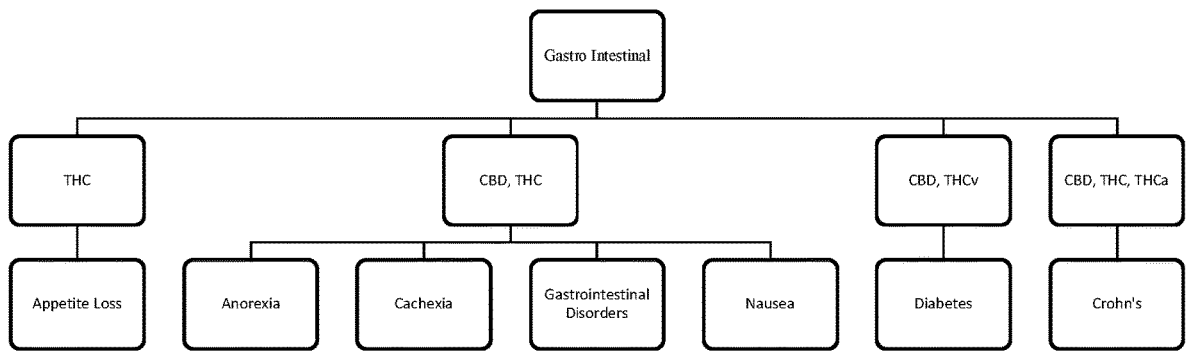
FIGS. 5A-5E are directed to flow charts showing various ailments that can be treated with one or more cannabinoids.
Figure 5B:
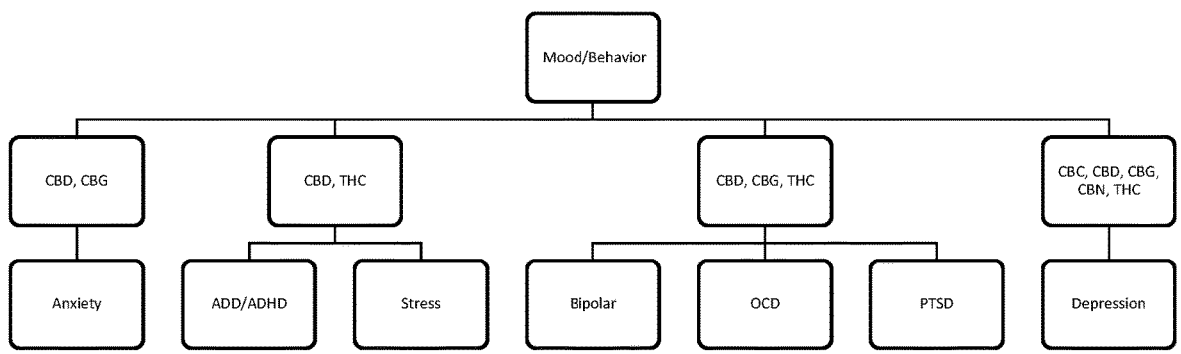
Figure 5C:
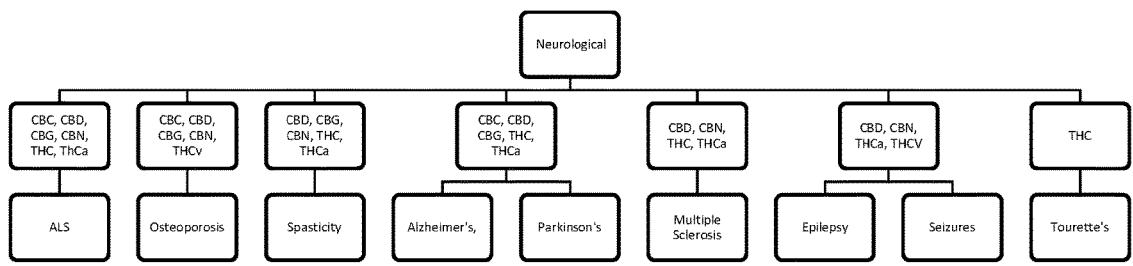
Figure 5D:
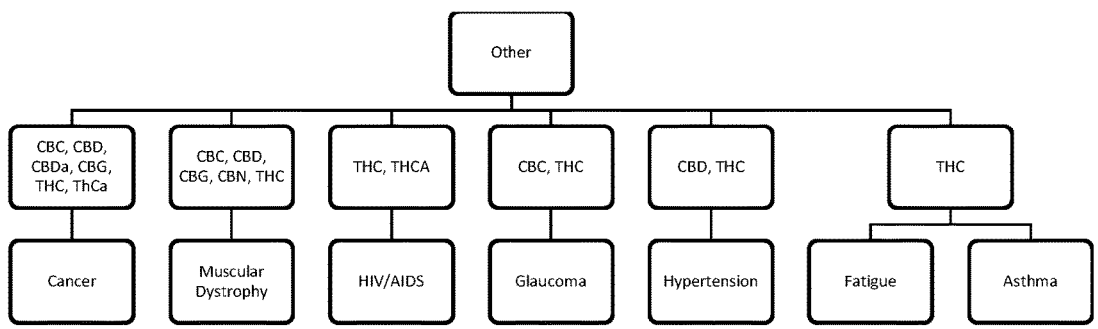
Figure 5E:
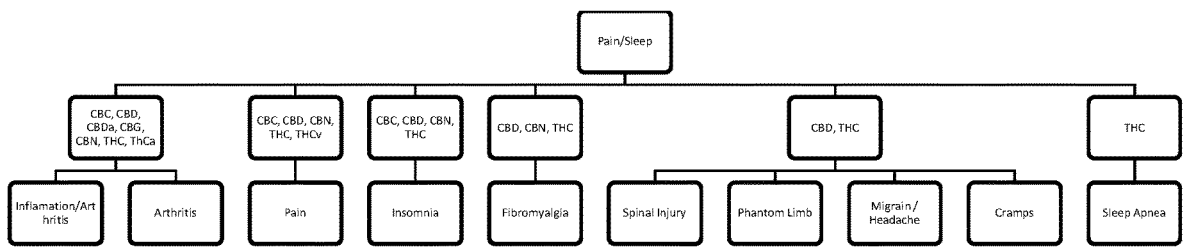
Figure 6A:
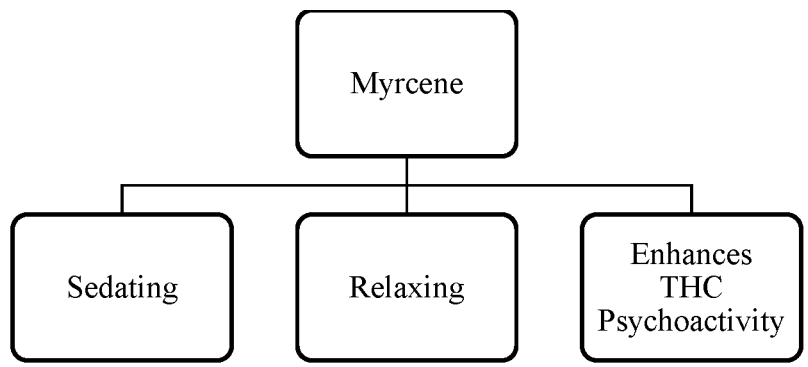
FIGS. 6A-6F are directed to flow charts showing various ailments that can be treated with one or more terpenes. The flow charts also show beneficial effects of various terpenes.
Figure 6B:
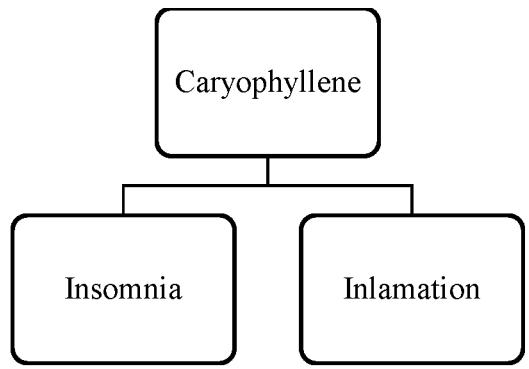
Figure 6C:
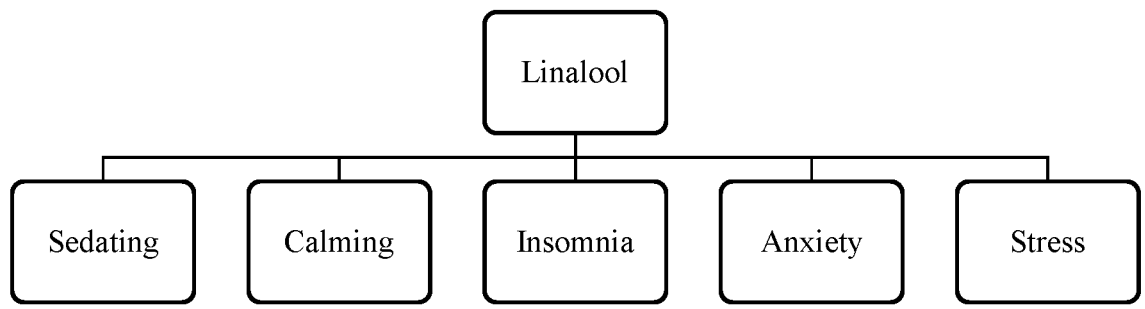
Figure 6D:
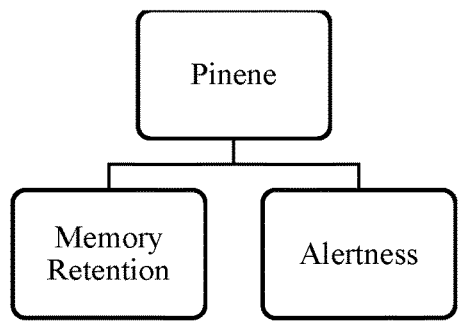
Figure 6E:
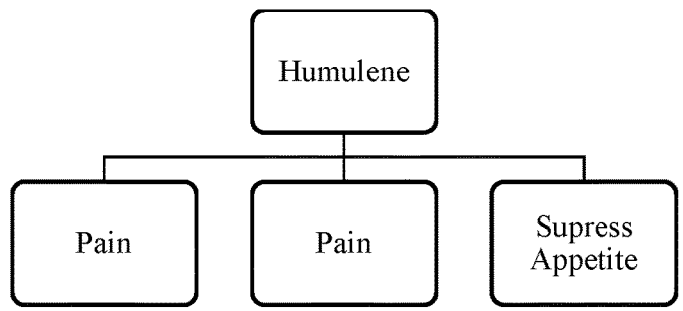
Figure 6F:
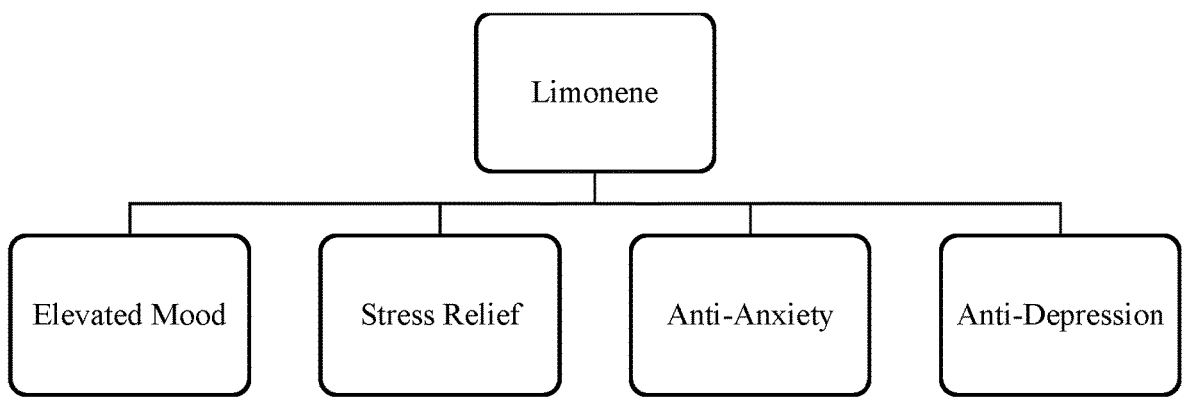
Figure 7A:
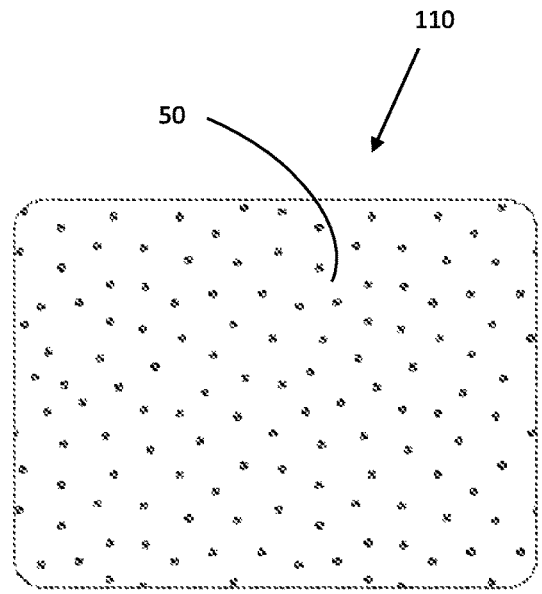
FIG. 7A illustrates the therapeutic side of a transdermal receiving pad and FIG. 7B illustrates the opposite side the transdermal receiving pad having an adhesive thereon.
Figure 7B:
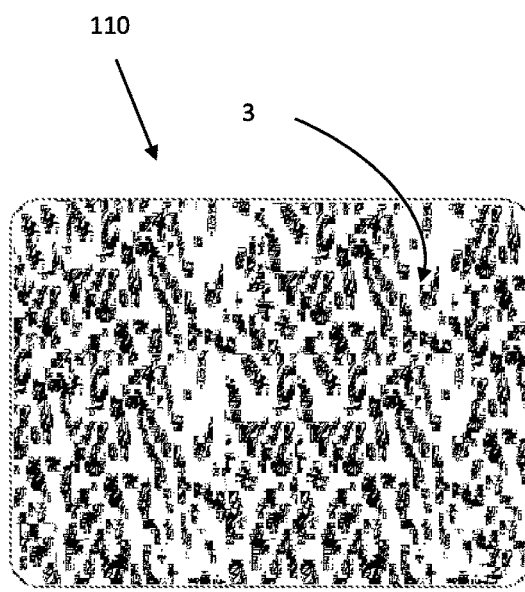
Figure 8A:
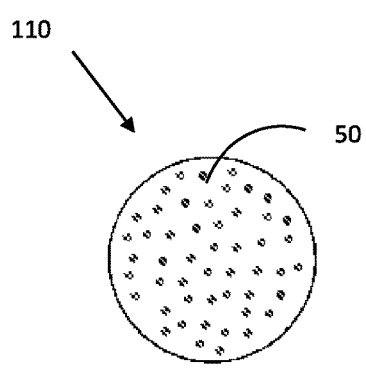
FIG. 8A illustrates the therapeutic side of a transdermal receiving pad and FIG. 8B illustrates the opposite side the transdermal receiving pad having an adhesive thereon.
Figure 8B:
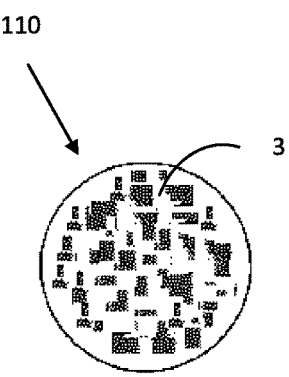
Figure 9A:
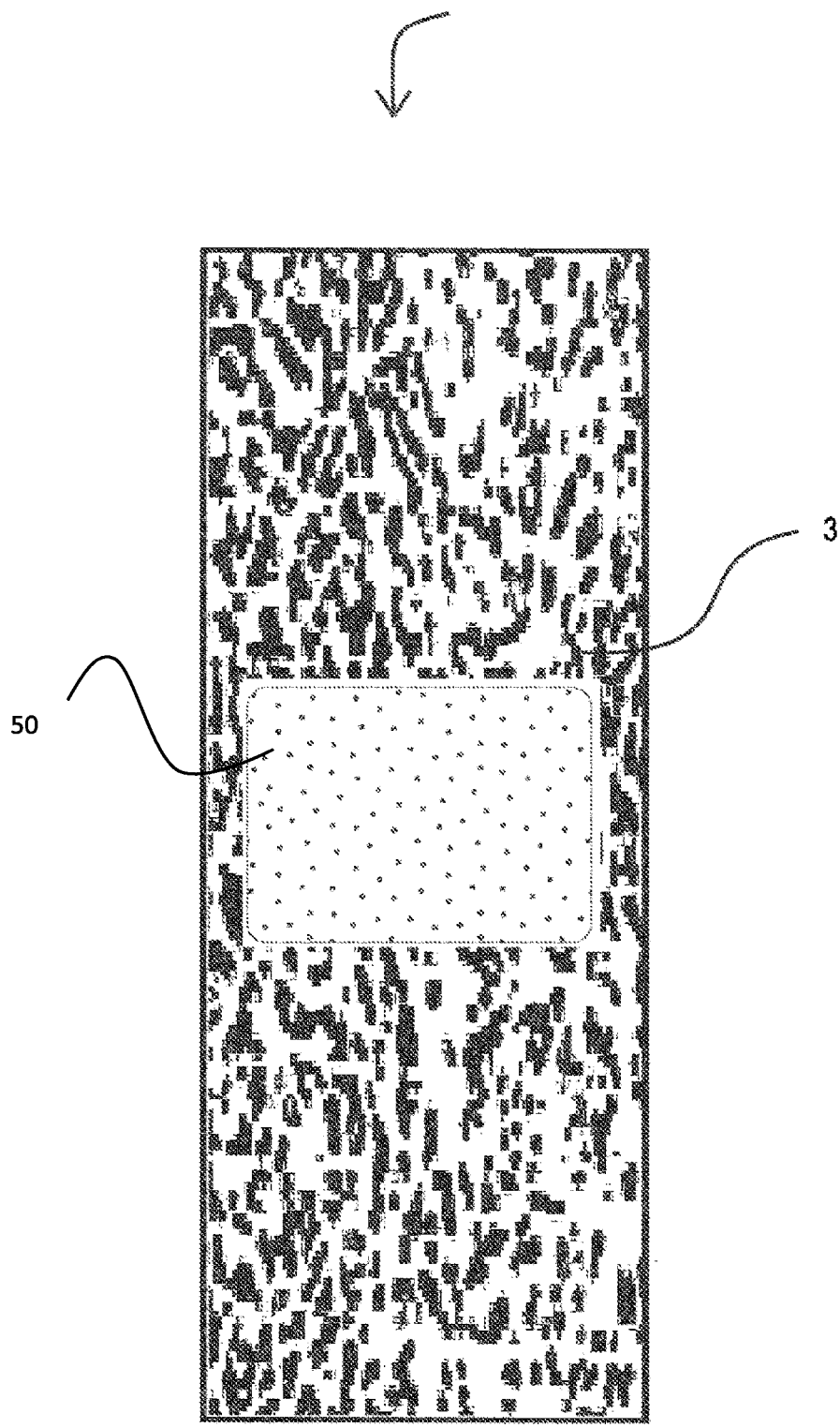
FIGS. 9A-9D show the back surface of the soft tissue mobilizing device having therapeutic transdermal receiving pads coupled thereon.
Figure 9B:
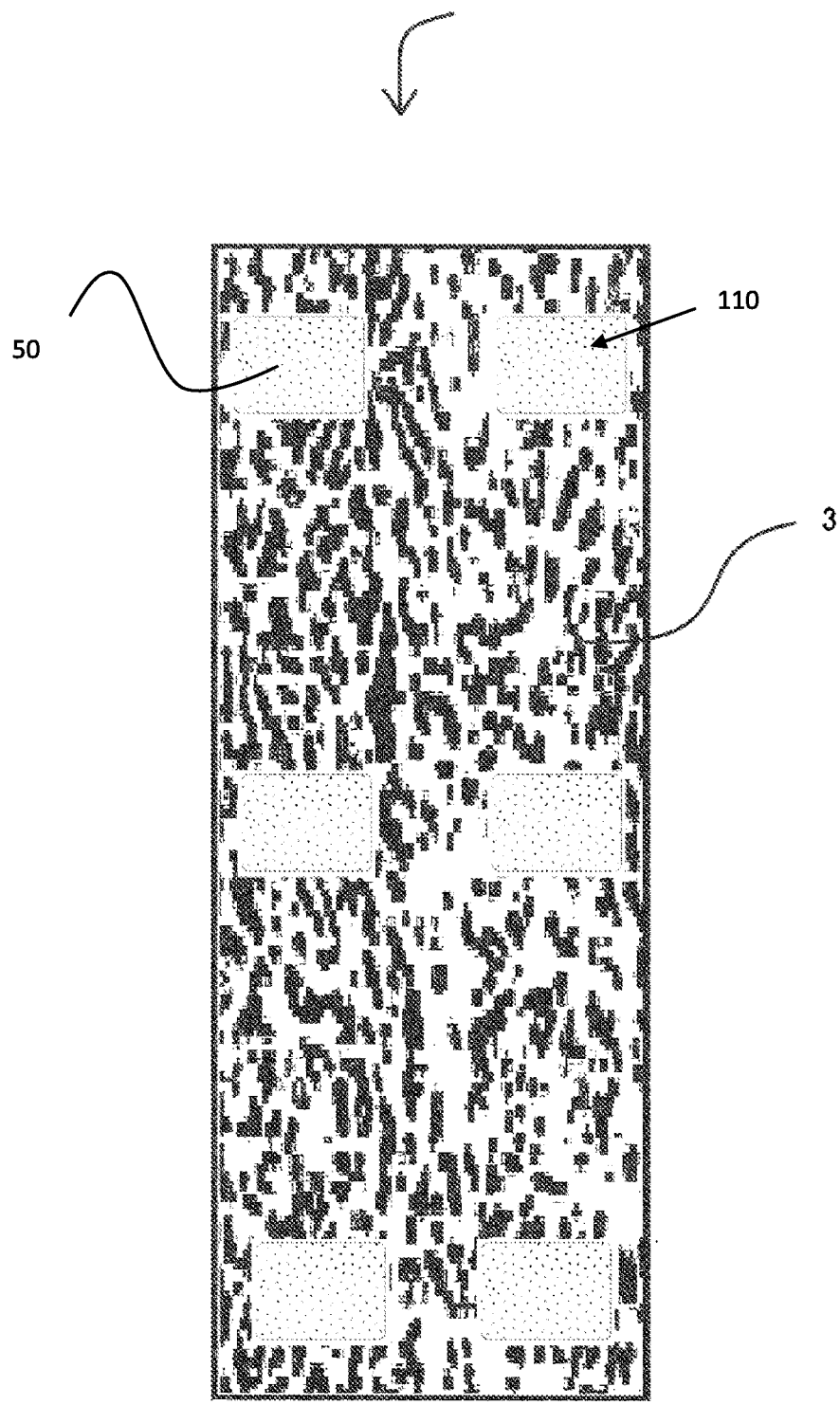
Figure 9C:
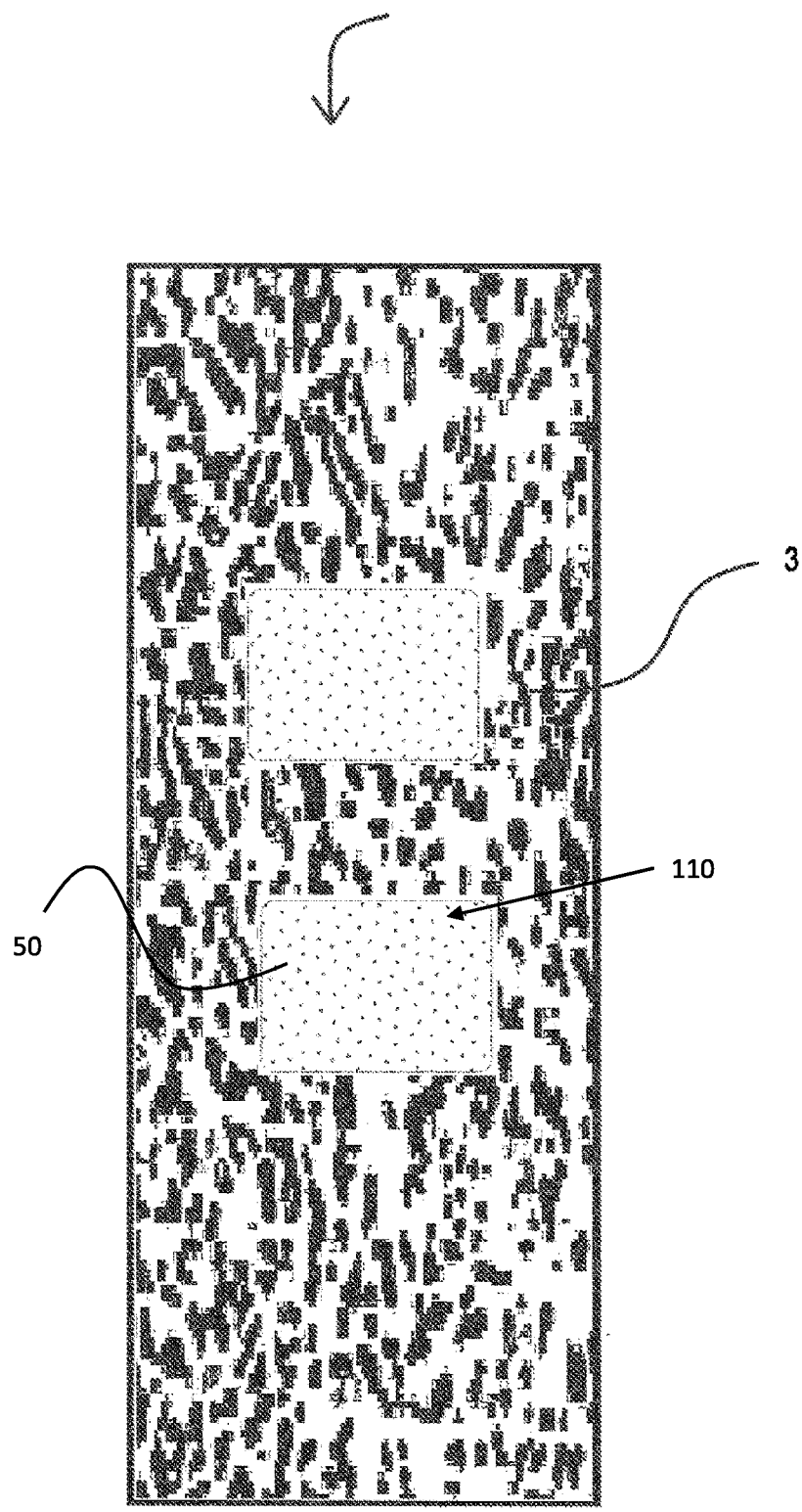
Figure 9D:
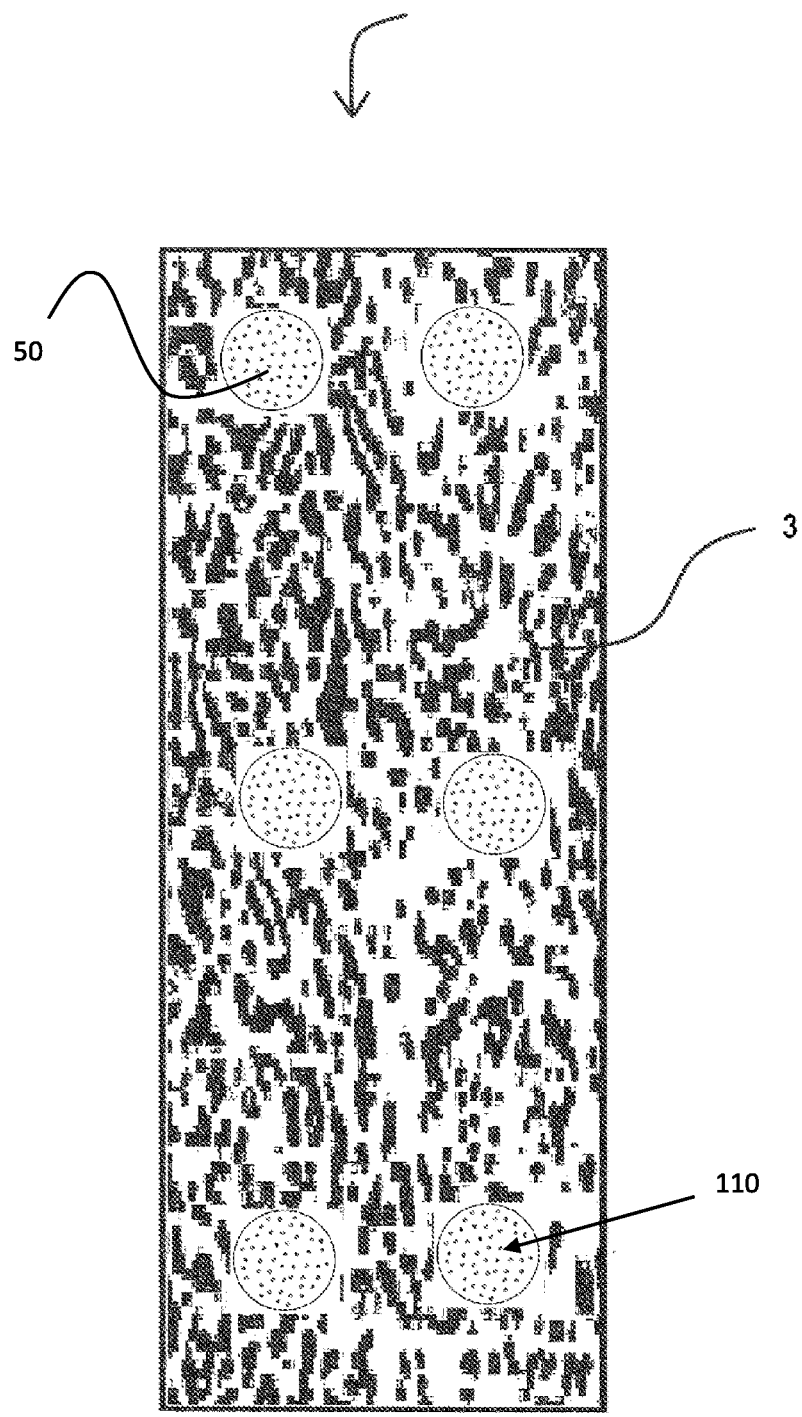
Figure 9E:
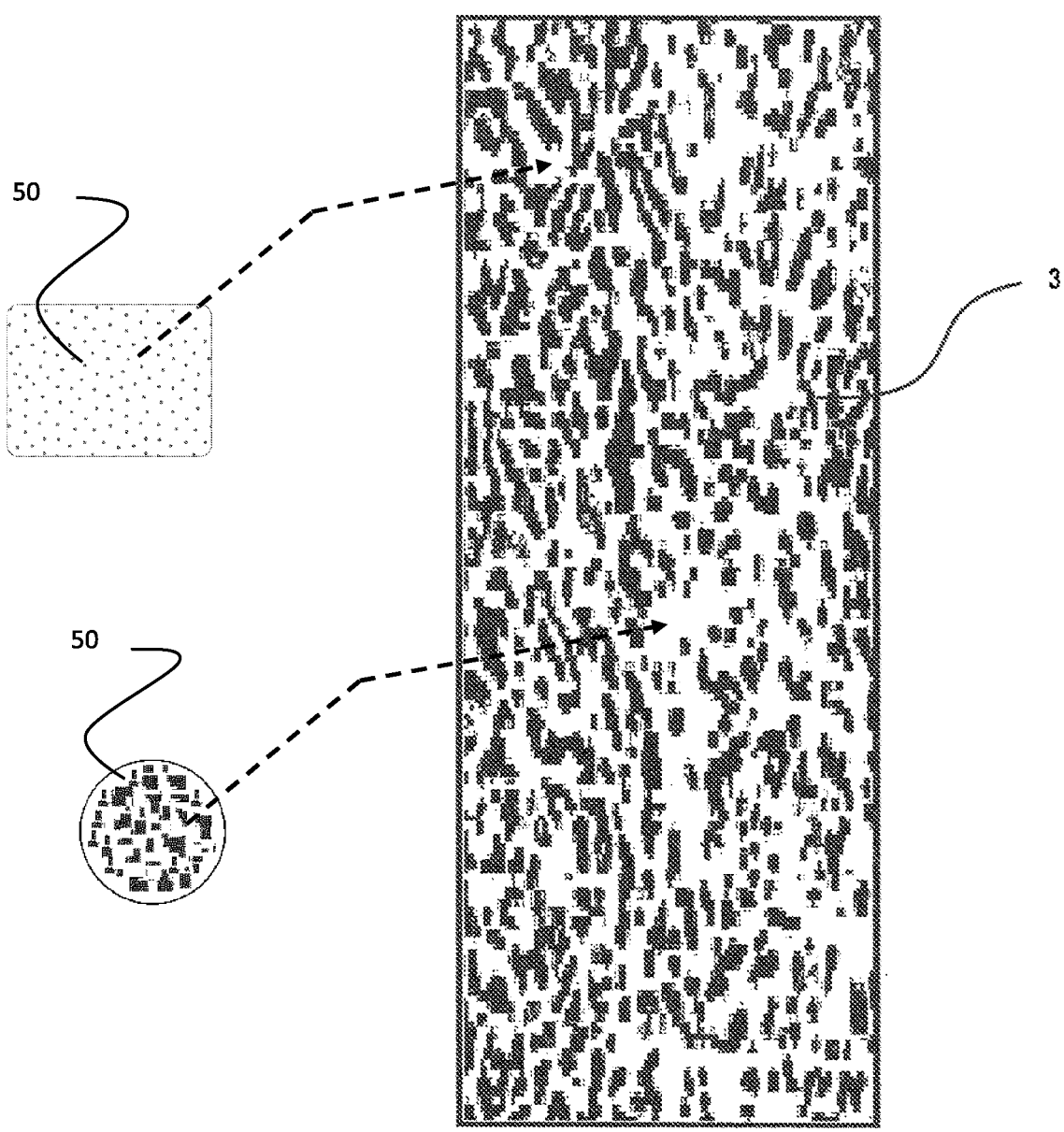
FIG. 9E shows one embodiment of the soft tissue mobilizing device configured to allow a therapist or user to choose where at least one therapeutic transdermal receding pad can be attached thereon.
Figure 10A:
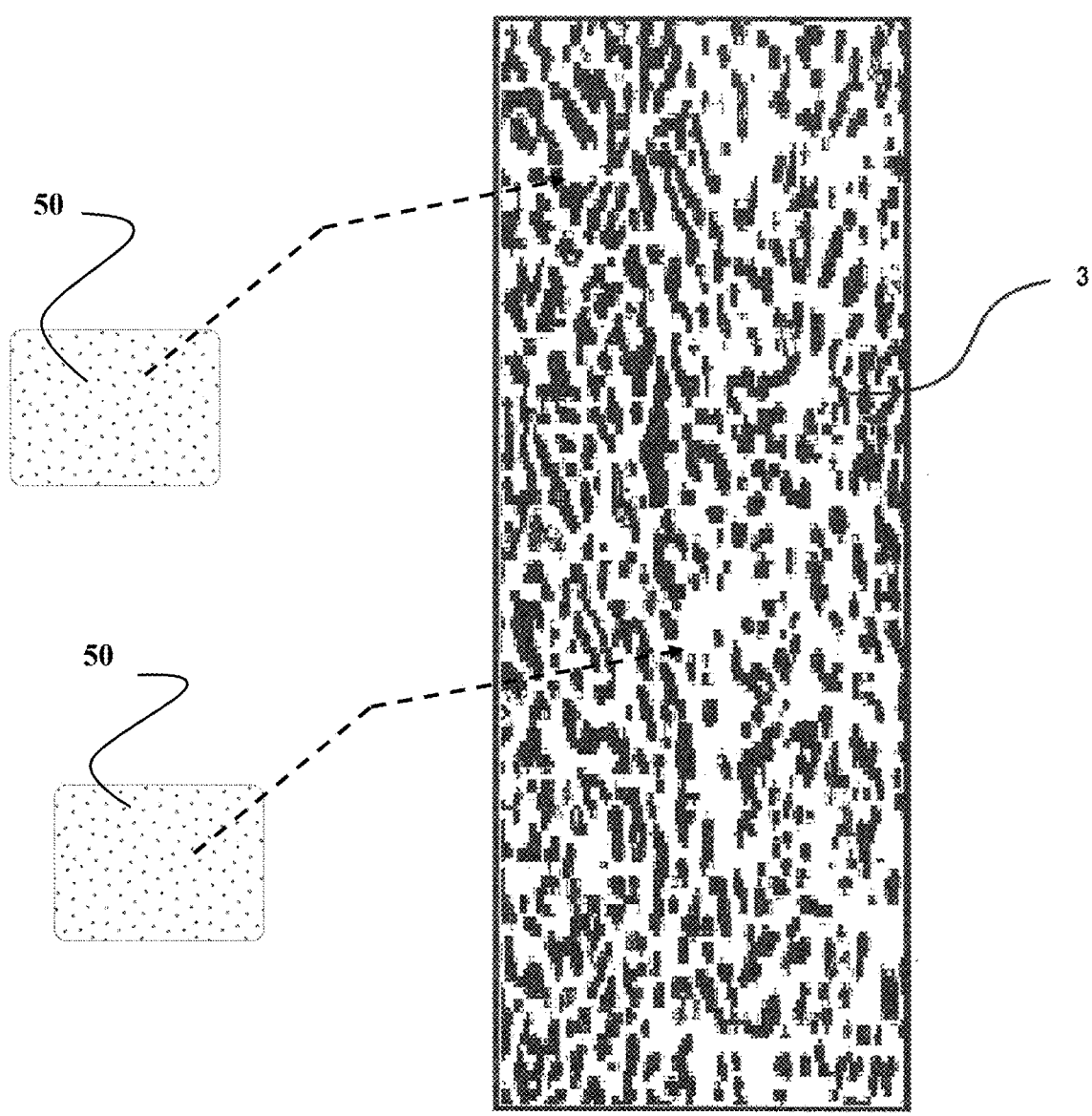
Figure 10B:
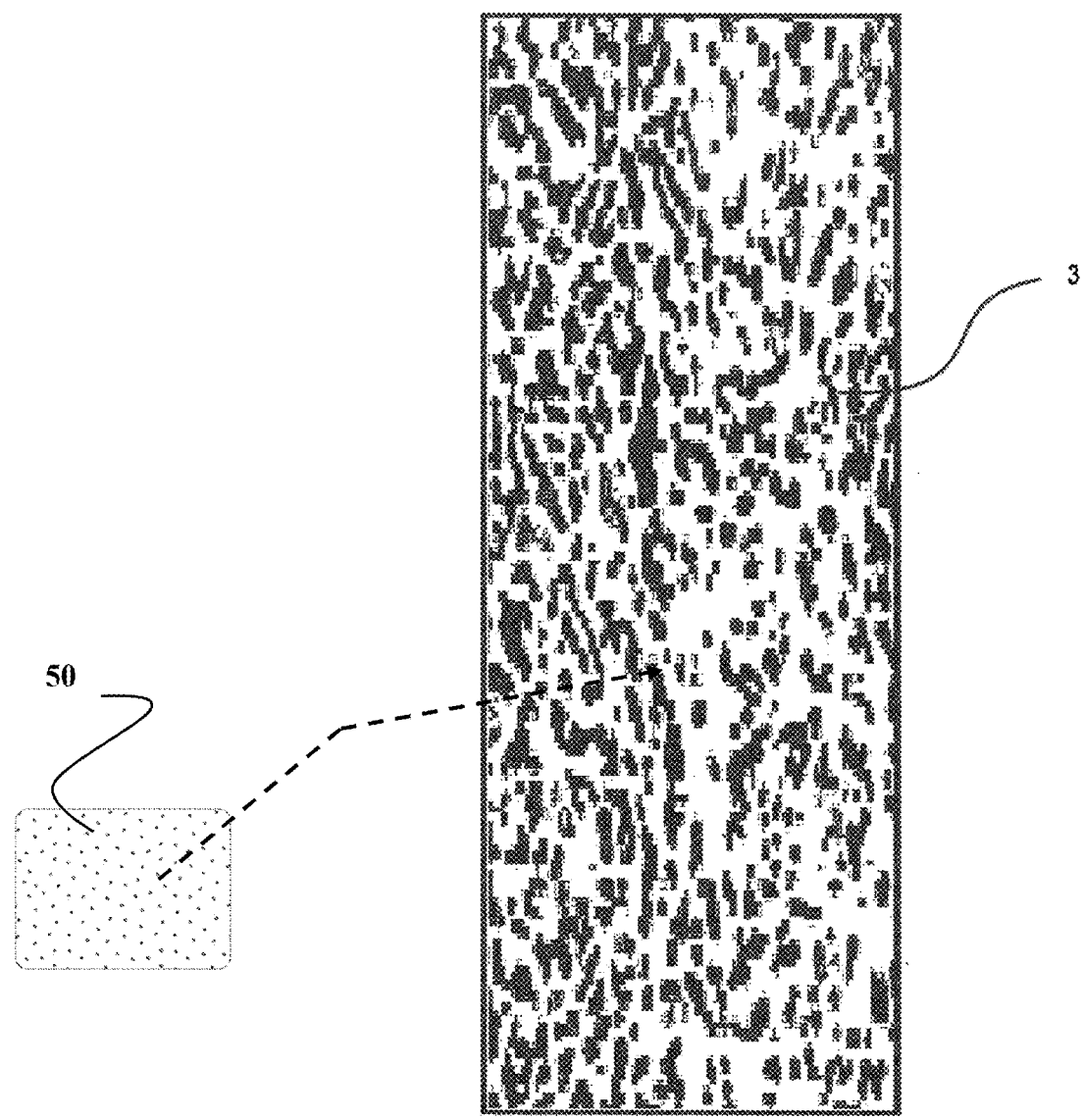
Figure 10C:
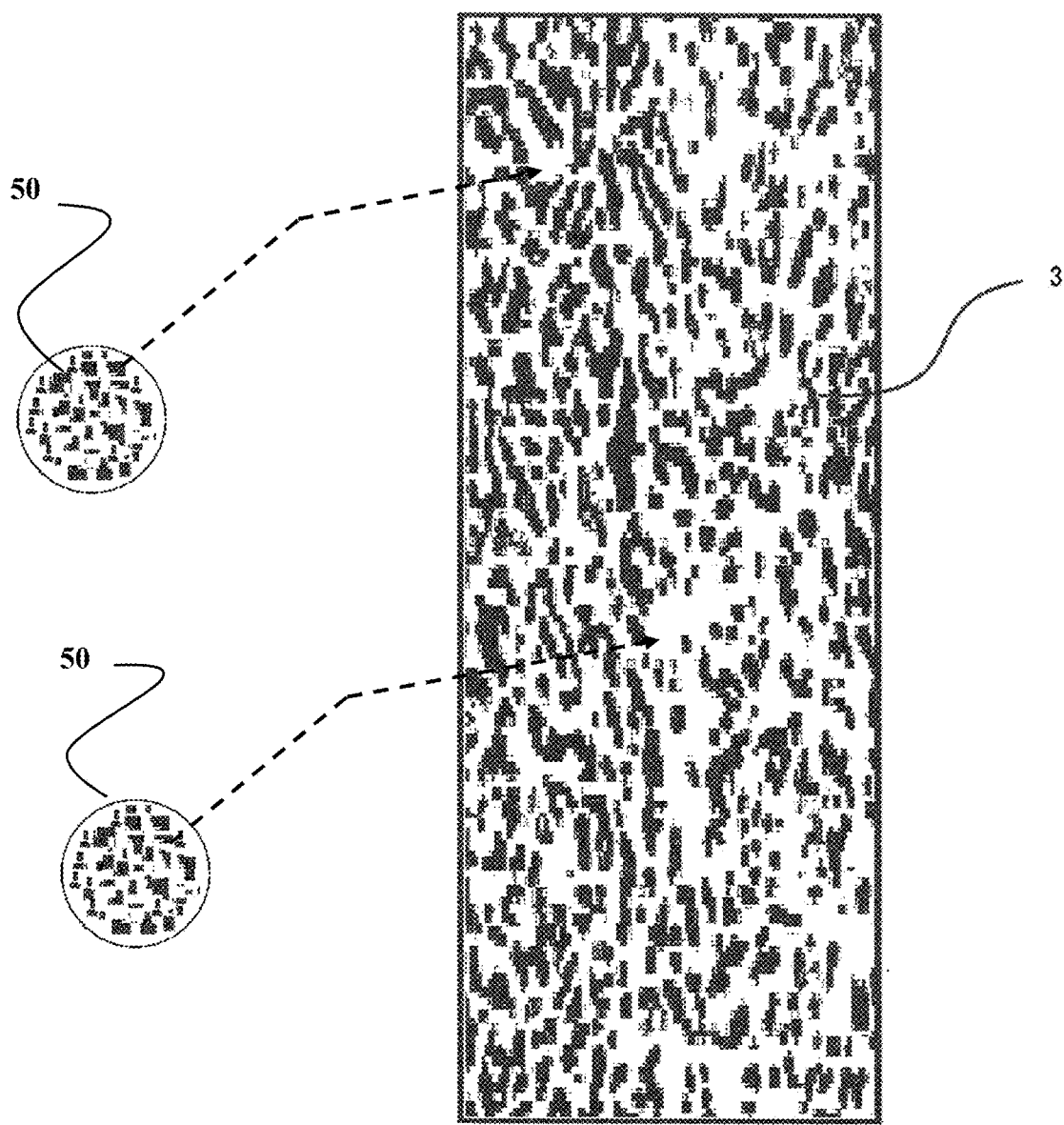
Figure 10D:
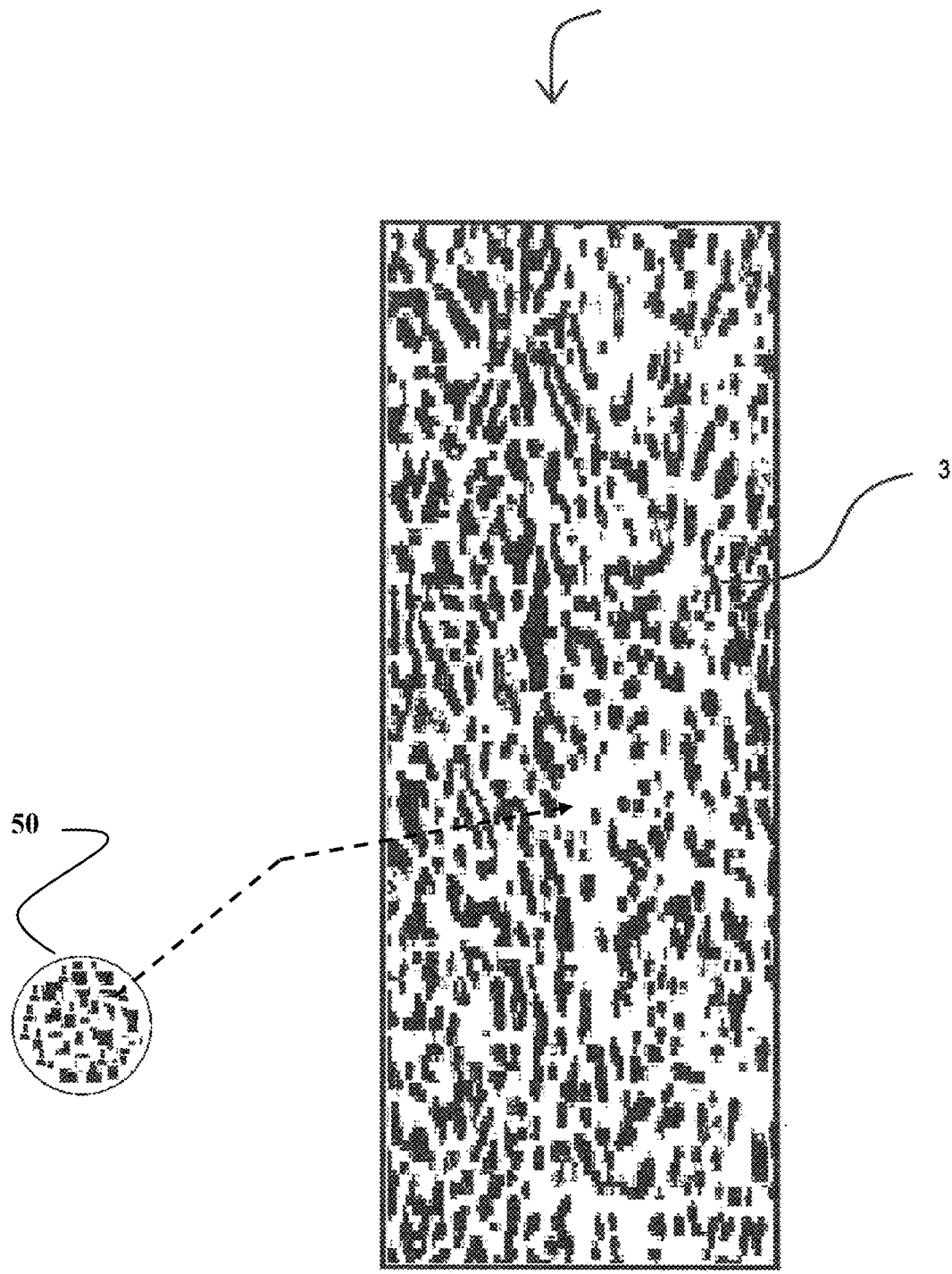
Figure 11:
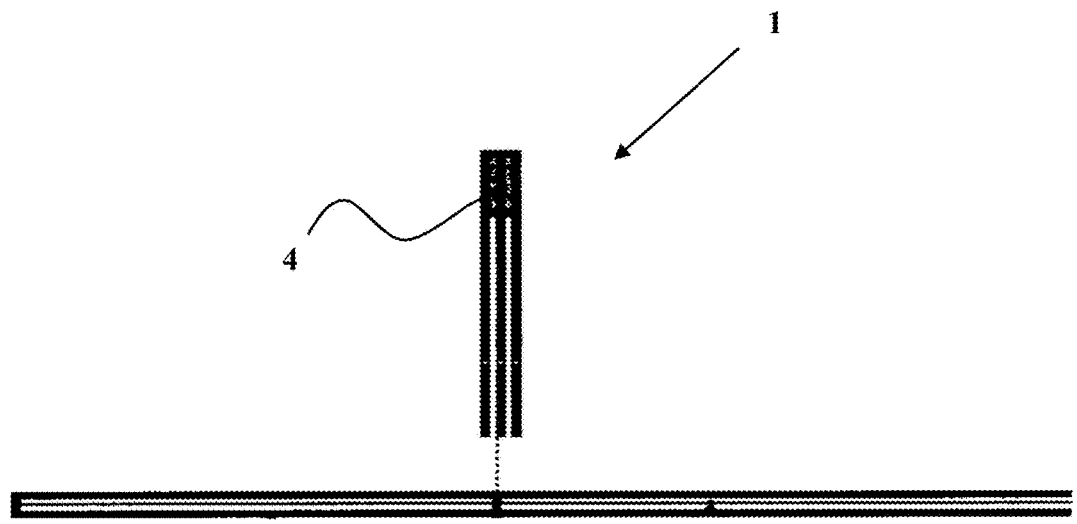
Figure 12:
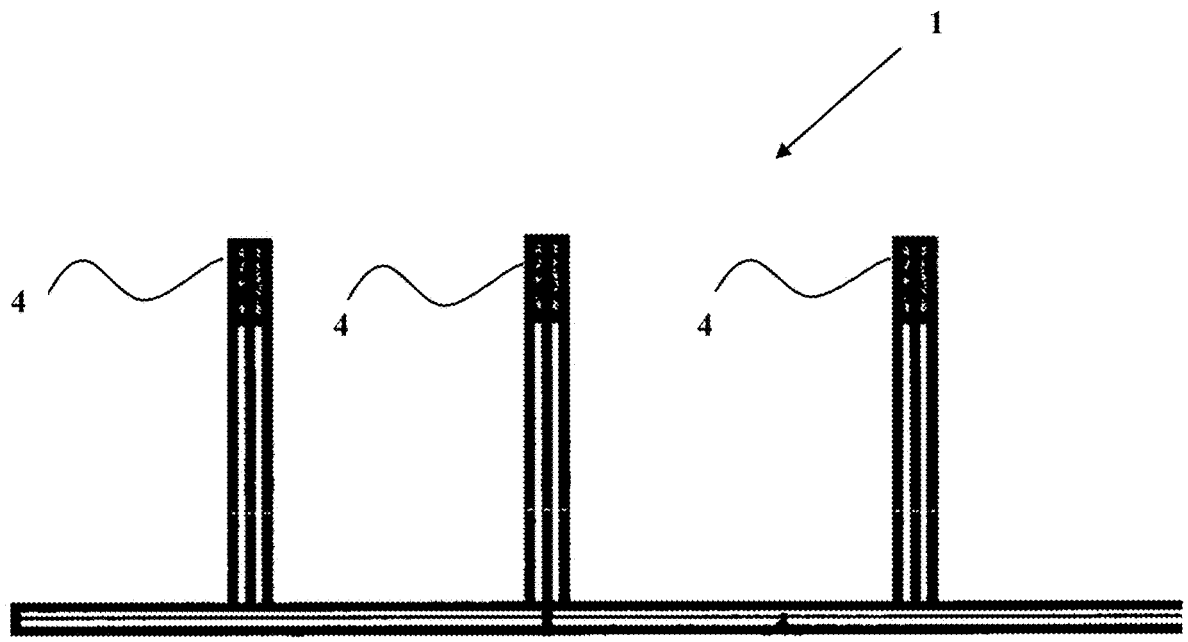
Figure 13:
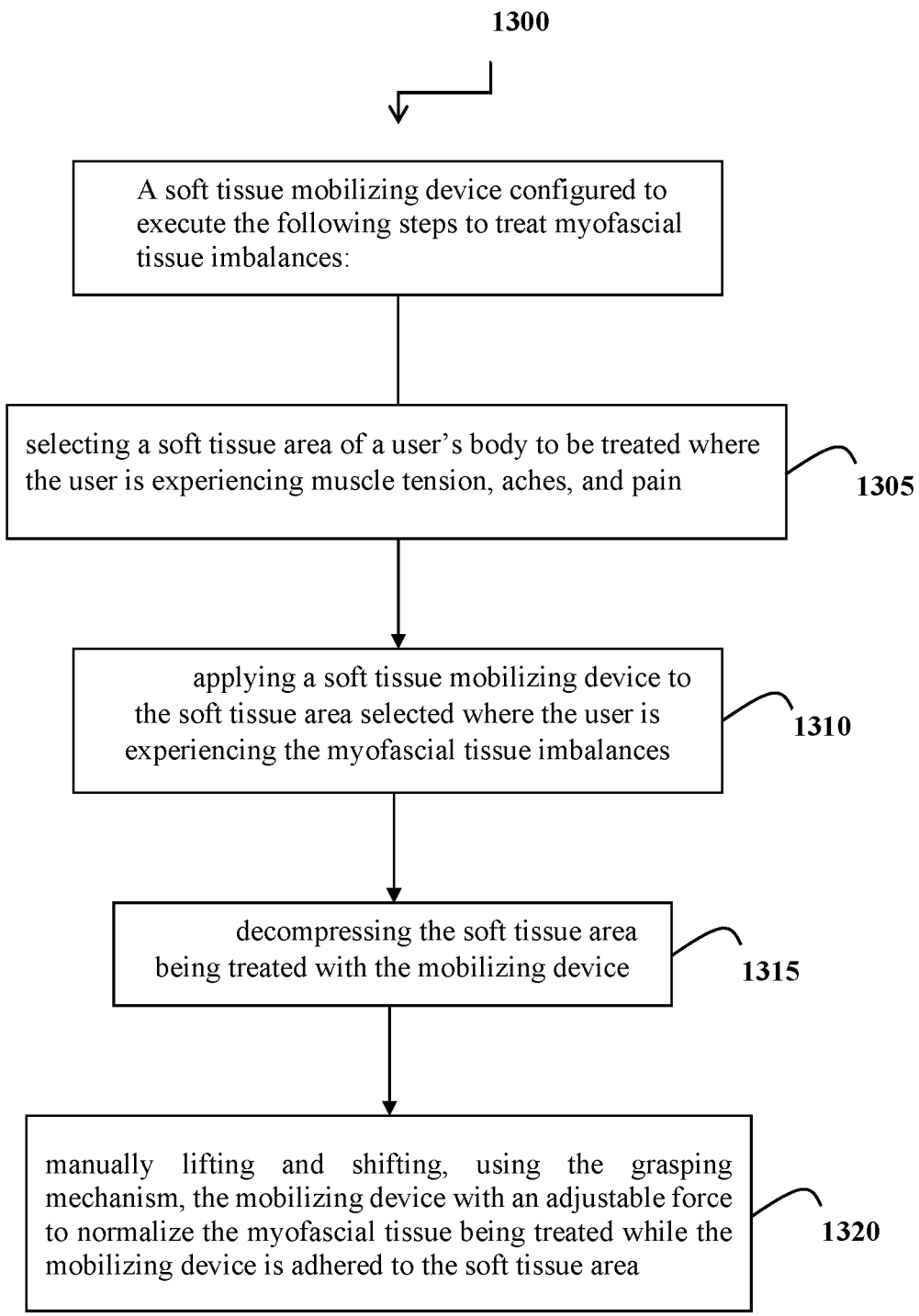
FIGS. 13-15 represent execution diagrams directed methods of treating myofascial tissue imbalances.

With reference to FIGS. 2-4, the therapy tape may comprise one or more stimulators (e.g., vibration element, pressure applicators, TENS devices, biofeedback devices, bio-impedance analysis devices, thermometers, pulse measurement devices, and/or the like) configured to provide stimulation to the skin to which the therapy tape is secured and/or to stimulate the transdermal features 50 of the present invention and/or to stimulate the therapeutic effects of a substance such a lotion, cream, gel and/or oil having a chemical composition and/or an active ingredient of cannabinoid and/or terpene that is applied directly to a user's skin prior to applying the soft tissue device directly to the soft tissue area of a user's body. As discussed herein, various embodiments of therapy tape may comprise a single vibration element, a plurality of vibration elements, a single pressure applicator, a plurality of pressure applicators, a single TENS electrode, a plurality of TENS electrodes, and/or the like. In various embodiments, a therapy tape may comprise one or more vibration elements and one or more pressure applicators. In yet other embodiments, a therapy tape may comprise one or more vibration elements and one or more TENS electrodes. In yet other embodiments, a therapy tape may comprise one or more pressure applicators and one or more TENS electrodes. In yet other embodiments, a therapy tape may comprise one or more vibration elements, one or more pressure applicators, and one or more TENS electrodes.

In various embodiments, the flossing motion and lifting of the soft tissue mobilizing device can help to stimulate the transdermal features of the present invention and/or help to stimulate the therapeutic effects of the substance applied to the user's skin prior to applying the mobilizing device. The substance can be comprised of a lotion, cream, gel and/or oil having a chemical composition and/or an active ingredient of cannabinoid and/or terpene.

As shown in FIG. 2, the therapy tape 41 may comprise a backing layer similar to that discussed herein, with one or more vibration elements 48 secured thereto. In various embodiments, the one or more vibration elements 48 may be secured relative to a top side of the backing layer 42, a bottom side of a backing layer 42 (e.g., between backing layer 42 and adhesive layer (not shown) or opposite adhesive layer relative to the backing layer 42). In another embodiment, the therapy tape 41 may define one or more apertures extending therethrough (e.g., through backing layer 42 and/or adhesive layer) in which the vibration elements 48 are secured. In various embodiments, therapy tape 41 may also comprise a backing layer 42 that includes transdermal features 50.

The one or more vibration elements 48 may comprise one or more vibration actuators configured to emit vibration pulses to a patient's skin to provide therapeutic sensations for the patient (e.g., pain relief, numbing, increased metabolic rate, and/or the like). In various embodiments, the one or more vibration elements 48 may be in electrical communication with a controller 100 (e.g., via electrical conduit 49) configured to emit power signals to each of the one or more vibration elements 48. In various embodiments, electrical conduit 49 may comprise one or more wires (e.g., solid and/or stranded), one or more printed electrical connectors (e.g., printed onto backing layer 42), and/or the like.

With reference now to FIG. 3A-3C, a therapy tape 51 may comprise one or more pressure applicators 58 (e.g., powered suction cups, compression sleeves, and/or the like) configured to provide pressure (e.g., negative pressure and/or positive pressure) to skin to which the therapy tape is secured 51. Each of the pressure applicators 58 may be in electrical and/or pneumatic communication with a controller 100 which may comprise a pump, an electrical actuator, and/or the like configured to provide pressure to each of the pressure applicators 58. For example, a conduit 59 extending from controller 100 to one or more of the pressure actuators 58 may comprise an electrical conduit (e.g., a wire) configured to transmit signals to each of the one or more pressure applicators 58 to cause each of the pressure applicators 58 to activate and provide pressure to the patient's skin and/or to the transdermal features 50. For example, each of the pressure applicators 58 may comprise actuators configured to apply a pressure to the patient's skin. In certain embodiments, the conduit 59 may comprise a pneumatic conduit (e.g., a tube) connecting a pump located at the controller 100 to each of the one or more pressure applicators 58. In such embodiments, the pump may be configured to pump air from the pressure applicators 58, thereby causing the pressure applicators to provide a pressure to the patient's skin. In various embodiments, therapy tape 51 may also comprise a backing layer that includes transdermal features 50.

FIG. 3B provides a side-view of a therapy tape 51 according to various embodiments. As shown in FIG. 3B, the pressure applicators 58 may additionally comprise one or more handles 54 extending therefrom. Each of the one or more handles 54 may have a configuration similar to handle 4 as discussed herein. However, the handles 54 may be secured directly to the pressure applicators 58. As shown in FIG. 3C, handles 54 may extend from a top portion 58 of the pressure applicators 58, opposite a bottom portion 58 configured to contact a patient's skin. The vibration applicators 48 may additionally comprise handles 54 as discussed herein.

With reference to FIG. 4, various therapy tape 61 embodiments may comprise a plurality of stimulators 68. As shown therein, therapy tape 61 may comprise a plurality of stimulators 68 comprising vibrating elements configured to apply vibration stimulation to the patient's skin, pressure applicators configured to apply pressure to the patient's skin, and/or transcutaneous electrical nerve stimulation devices (TENS devices) configured to apply electrical stimulation to a patient's skin and/or configured to apply vibration/pressure/electrical stimulation to the transdermal features 50. Each of the stimulators 68 may be in electrical and/or pneumatic communication with a controller 100 via a conduit 69. As shown in FIG. 4, the therapy tape 61 may comprise one or more handles 64 similar to handle 4. Although not shown, therapy tape 61 may be configured to accept one or more detachable handles as discussed herein. In such embodiments, the therapy tape 61 may comprise one or more connecting portions 36 configured to engage one or more detachable handles 37. In various embodiments, therapy tape 61 may also comprise a backing layer that includes transdermal features 50.

Method of Use

Various embodiments of the described therapy tape may be utilized to provide therapeutic treatment of one or more ailments of a patient. For example, the described therapy tape may be configured to increase blood and/or other fluid flow to various portions of a patient's body, to relieve muscle pressure in various portions of a patient's body, to discourage formation of scar tissue, to enhance the transdermal features of the tape and/or the like.

In use, therapy tape having one or more handles secured thereto may be adhered to a patient's skin. In various embodiments, a length of therapy tape may be removed from a roll of therapy tape (e.g., by cutting a selectable length of therapy tape from the roll of therapy tape) and may be adhered to a patient's skin (See FIGS. 16A-6B and 17A-17E). In embodiments in which the adhesive layer of the therapy tape is heat activated by a patient's body heat after application of the tape to the patient.

Once the therapy tape is securely adhered to the patient's skin, a tensile force may be applied to one or more of the handles (e.g., by pulling one or more of the handles) to lift a portion of the patient's skin adjacent to the one or more handles. In various embodiments, the tensile force may be applied at least substantially normal to the surface of the patient's skin (e.g., at least substantially perpendicular to the patient's skin), however the tensile force may be applied at an acute angle relative to the patient's skin (e.g., between 0-90 degrees relative to the patient's skin). As just one non-limiting example, the tensile force may be applied at an angle between about 45-90 degrees relative to the patient's skin. The tensile force may be applied as a part of a multi-way skin and/or tissue massage and/or manipulation treatment. For example, the handles may be pulled and/or twisted, and the tape may be compressed during the treatment. For example, the handles may be pulled in any direction (e.g., in a direction aligned at least in part with the length of the tape, in a direction aligned at least in part with the width of the tape, in a direction normal to the tape, and/or any directions in between). The one or more handles may also be twisted (e.g., around an axis normal to the tape, around an axis parallel with the length of the tape, around an axis parallel with the width of the tape, and/or any axis in between).

In embodiments comprising detachable handles and a connecting portion, the therapy tape may be applied as discussed above. Once applied to a patient's skin, one or more of the detachable handles may be secured relative to one or more connecting portions. Once secured, a tensile force may be applied to one or more of the detachable handles (e.g., by pulling one or more of the detachable handles) to lift the therapy tape and an adjacent portion of the patient's skin.

In various embodiments, a substance such a lotion, cream, gel and/or oil having a chemical composition and/or an active ingredient of cannabinoid and/or terpene can be applied directly to a user's skin prior to applying the soft tissue device directly to the soft tissue area of a user's body.

Transdermal Delivery Features and Topical Application

Referring to FIGS. 8A-8B, 9A-9B, and 10A-10E, the soft tissue device Jan. 11, 2021/31/41/51/61 includes a back surface 2 that is comprised of at least one transdermal pad 110 and/or at least one transdermal receiving pad 110. In one embodiment of the present invention, the transdermal pad 110 and/or the transdermal receiving pad 110 each have an adhesive side 3. In another embodiment, the transdermal pad 110 and/or transdermal receiving pad 110 each have a substance/medicated/therapeutic side 50.

In various embodiments, the substance side 50 of the transdermal receiving pad 110 is suitably configured to receive a substance/medication 50 of choice selected by a user that is adapted to be absorbed through the user's/mammal's skin. In another embodiment, the substance side 50 of the transdermal pad 110 includes a preselected substance 50 at the time of purchase that is also adapted to be absorbed through the user's skin to promote wellness.

In various embodiments, wellness refers to an active process of becoming aware of and making choices toward a healthy and fulfilling life for oneself. Wellness is more than being free from illness, disease or infirmity, it is a dynamic process of change and growth.

In use, an effective amount of a skin permeation enhancer is placed on the back surface of the device or the pad. The skin permeation enhancer has an HLB of about 6-30.

Optionally, the user can be, but is not limited to, a therapist, physician, patient, athlete, trainer or wellness provider.

In various embodiments, a preselected area of the back surface of the present invention is comprised of at least one transdermal pad 110 configured to receive at least one substance 50 that is adapted to be absorbed through a user's skin. In other embodiments, a user can select different areas on the back surface of the pad 110 to advantageously attach at least one transdermal pad 110 thereon that is configured to receive or come with at least one substance 50 suitably adapted to be absorbed through a user's skin.

In one embodiment, the substance 50 on the pad 110 is comprised of at least one cannabinoid and/or terpene. In another embodiment, the cannabinoid and/or terpene is comprised of an oil, a gel or a lotion.

In another embodiment, the pad includes a reservoir for holding the therapeutic substance. In another embodiment, the reservoir is comprised of a cavity, matrix material, or a film. In a further embodiment, the matrix material is comprised of open pore material, open weave fabric or a membrane.

In various embodiments, the cannabinoid is comprised of one or a combination of tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), and cannabicitran (CBT).

In another embodiment, the CBD is in the range of 10 mg to 80 mg, and the amount of THC is in the range of 2 mg to 25 mg.

In various embodiments of the present invention, the therapeutic substance is cannabidiol (CBD). In other embodiments, the CBD is comprised of CBD derived from lemon peel, orange peel, tree bark and/or hops.

In use, an effective amount of the therapeutic substance is placed onto the transdermal preparation pad to help promote health and wellness. In various embodiments, the effective amount of therapeutic substance is in the range of 2 mg to 80 mg. In various embodiments, the substance is at least one cannabinoid.

In another embodiment, the amount of the CBD is in the range of 10 mg to 160 mg, and the amount of THC is in the range of 2 mg to 25 mg.

In an alternative embodiment, at least one transdermal sector will include a combination of CBD derived from lemon and orange peel.

In an alternative embodiment, at least one transdermal sector will include a combination of CBD oil or CBD gel derived from lemon and orange peel.

In use, the topical transdermal device and pad is maintained in contact with the user's skin for an effective period of time to further help promote health and wellness. The effective period of time can be in the range of 15 minutes to 12 hours.

In use, the manual lifting and shifting of the device by hand via a flossing (i.e., pulling, shifting, stretching) motion helps to not only remove and/or break up fibrous adhesions until relief occurs but also helps to promote an increase blood circulation when using the transdermal device. An increase in circulation around muscle and myofascial tissue helps to encourage a rise in muscle and tissue temperature which can advantageously lead to an increase in the permeation of the therapeutic substance.

An increase in blood circulation and muscle/tissue temperature can also help to increase the penetration and delivery of the active ingredient(s) in the therapeutic substance. Similarly, an increase in blood circulation and muscle/tissue temperature can also help to increase the penetration and delivery rate of the active ingredient(s) in the therapeutic substance. Further, an increase in blood circulation and muscle temperature helps with improved body function and wellness, and helps to improve the process of promoting health, relief, healing and well-being in mammals. Importantly, these statements are not intended in any way, shape or form to represent that the present invention and its unique features are configured to diagnose, treat, or cure any disease in mammals.

Most of the cells in the human body are only capable of directly absorbing particles which are 60 to 80 nanometers in size. The cannabinoid particles in most commercially available hemp oils, no matter how high the purported quality, is about 2000 nanometers.

In various embodiments of the present invention, the cannabinoid oil is comprised of water-soluble cannabinoid oil derived by formulations that include: microemulsions, liposomes and nanoemulsions. The size of the cannabinoid particles generated from the above referenced formulation will have diameters in the range between 3 to 100 nanometers. This beneficial range will advantageously increase the bioavailability of the cannabinoid oil since mammals will be better able to absorb the water solvable oil through their skin.

In various embodiments, the terpene oil is comprised of water-soluble oil derived by formulations that include: microemulsions, liposomes and nanoemulsions. The size of the terpene particles generated from the above referenced formulation will have diameters in the range between 3 to 100 nanometers. This range will advantageously increase the bioavailability of the terpene oil since users will be better able to absorb the water solvable oil through their skin.

In an optional embodiment of the present invention, an effective amount of a skin permeation enhancer is placed on the back surface of the device. The skin permeation enhancer of the present invention has an HLB of about 6-30.

In another embodiment, the amount of the CBD is in the range of 10 mg to 160 mg, and the amount of THC is in the range of 2 mg to 25 mg.

In another embodiment, the amount of the CBN is in the range of 10 mg to 65 mg.

In a further embodiment, the amount of CBN is in the range of 10 mg to 65 mg, and the amount of THC is in the range of 2 mg to 25 mg.

In various embodiments of the present invention, the cannabinol oil is comprised of water-soluble cannabinol oil derived by formulations that include: microemulsions, liposomes and nanoemulsions. The size of the cannabinol particles generated from the above referenced formulation will have diameters in the range between 3 to 100 nanometers. This range will advantageously increase the bioavailability of the cannabinol oil since users will be better able to absorb the water solvable oil through their skin.

In various embodiments, the terpenes of the present invention are comprised of at least one or a combination of myrcene, caryophyllene, limonene, and linalool.

In another embodiment, the terpene/terpenoid includes myrcene. Myrcene, or β-myrcene, is an olefinic natural organic compound. It is classified as a hydrocarbon, more precisely as a monoterpene. Terpenes are dimers of isoprene, and myrcene is one of the most important. It is a component of the essential oil of several plants including bay, *cannabis*, ylang-ylang, wild thyme, mango, parsley and hops. It is produced mainly semi-synthetically from myrcia, from which it gets its name. It is a key intermediate in the production of several fragrances. α-Myrcene is the name for the structural isomer 2-methyl-6-methylene-1,7-octadiene, which is not found in nature and is little used. Its IUPAC name is 7-methyl-3-methylene-1,6-octadiene.

Myrcene has an analgesic effect and is likely to be responsible for the medicinal properties of lemon grass tea. It has anti-inflammatory properties through Prostaglandin E2. β-Myrcene is reported to have anti-inflammatory properties, and is used to treat spasms, sleep disorders and pain. Myrcene appears to lower resistance across the blood to brain barrier, allowing itself and many other chemicals to cross the barrier more effectively.

In one embodiment, the amount of the myrcene is in the range of 5 mg to 125 mg.

In another embodiment, the myrcene is derived from fruits and/or herbs.

In another embodiment of the present invention, the myrcene is derived from mangoes, basil, thyme and lemongrass.

In another embodiment, the terpene/terpenoid includes caryophyllene, also known as β-caryophyllene. Caryophyllene is a natural bicyclic sesquiterpene that is a constituent of many essential oils, including clove, *cannabis*, rosemary and hops. It is usually found as a mixture with isocaryophyllene (the cis double bond isomer) and a-humulene, a ring-opened isomer. Caryophyllene is notable for having a rare cyclobutane ring.

Caryophyllene is known to be one of the compounds that contribute to the spiciness of black pepper. In a study conducted by the Swiss Federal Institute of Technology, (3-caryophyllene was shown to be selective agonist of cannabinoid receptor type-2 (CB2) and to exert significant cannabimimetic, anti-inflammatory effects in mice. Antinociceptive, neuroprotective, anxiolytic, antidepressant and anti-alcoholic activity have been tied to caryophyllene. Because β-caryophyllene is an FDA approved food additive, it is considered the first dietary cannabinoid.

In one embodiment of the present invention, the amount of the caryophyllene is in the range of 5 mg to 130 mg.

In one embodiment, the terpene/terpenoid includes limonene. Limonene is a colorless liquid hydrocarbon classified as a cyclic terpene. The more common D-isomer possesses a strong smell of oranges and a bitter taste. It is used in chemical synthesis as a precursor to carvone and as a solvent in cleaning products. Limonene is a chiral molecule. Biological sources produce one enantiomer—the principal industrial source—citrus fruit, contains D-limonene ((+)-limonene), which is the (R)-enantiomer (CAS number 5989-27-5, EINECS number 227-813-5). Racemic limonene is known as dipentene. Its IUPAC name is 1-methyl-4-(1-methylethenyl)-cyclohexene.

Limonene has a history of use in medicine, food and perfume. It has very low toxicity, and humans are rarely allergic to it. Limonene is used as a treatment for gastric reflux and as an anti-fungal agent. Its ability to permeate proteins makes it a useful treatment for toenail fungus. Limonene is also used for treating depression and anxiety. It is reported to assist in the absorption of other terpenoids and chemicals through the skin, mucous membranes and digestive tract. It has immunostimulant properties. It is also used as botanical insecticide The principle metabolites of limonene are (+)- and (−)-trans-carveol, a product of 6-hydroxylation) and (+)- and (−)-perillyl alcohol, a product of 7-hydroxylation by CYP2C9 and CYP2C19 cytochromes in human liver microsomes. The enantiomers of perillyl alcohol have been researched for possible pharmacological possibilities as dietary chemotherapeutic agents. They are considered novel therapeutic options in some CNS neoplasms and other solid tumors, especially for treatment of gliomas. The cytotoxic activities of perillyl alcohol and limonene metabolites are likely due to their antiangiogenic properties, hyperthermia inducing effects, negative apoptosis regulation and effect on Ras pathways.

In one embodiment, the amount of the limonene is in the range of 10 mg to 90 mg.

In another embodiment, the limonene is derived from fruits.

In another embodiment, the limonene is derived from citrus fruits.

In another embodiment, the terpene/terpenoid includes linalool. Linalool is a naturally occurring terpene alcohol chemical found in many flowers and spice plants with many commercial applications, the majority of which are based on its pleasant scent (floral and slightly spicy). It is also known as B-linalool, linalyl alcohol, linaloyl oxide, p-linalool, allo-ocimenol, and 3,7-dimethyl-1,6-octadien-3-ol. Its IUPAC name is 3,7-dimethylocta-1,6-dien-3-ol.

More than 200 species of plants produce linalool, mainly in the families Lamiaceae, Lauraceae and Rutaceae. It has also been found in some fungi. Linalool has been used for thousands of years as a sleep aid. Linalool is an important precursor in the formation of Vitamin E. It has a history of use in the treatment of both psychosis and anxiety, and as an anti-epileptic agent. It also provides analgesic pain relief. Its vapors have been shown to be an effective insecticide against fleas, fruit flies and cockroaches. Linalool is used as a scent in an estimated 60-80% of perfumed hygiene products and cleaning agents including soaps, shampoos and lotions.

In one embodiment, the amount of the linalool is in the range of 5 mg to 125 mg.

In various embodiments, at least one transdermal sector includes a combination of at least one terpene and at least one cannabinoid disposed thereon.

In use, an effective amount of at least one substance is placed onto the transdermal sector to help promote health and wellness, calmness and sleepiness.

In use, the transdermal sectors are maintained in contact with the user's skin for an effective period of time to further help promote health and wellness, calmness and sleepiness. The effective period of time can be in the range of 30 minutes to 4 hours.

In another embodiment, the transdermal pad will include an adequate amount of the water-soluble cannabinoid oil. In various embodiments, the CBD amount is in the range of 10 mg to 80 mg, and the amount of the THC is in the range of 2 mg to 25 mg.

In various embodiments, the transdermal application of the present invention can be carried out by topical application. For example, a substance such a lotion, cream, gel and/or oil having a chemical composition and/or an active ingredient of cannabinoid and/or terpene can be applied directly to a user's skin prior to applying the soft tissue device directly to the soft tissue area of a user's body. The applied device will help to decompress the soft tissue area being treated and the substance applied to the user's skin will help to extend the widespread potential therapeutic benefits of cannabinoids and/or terpenes.

Figure 14:
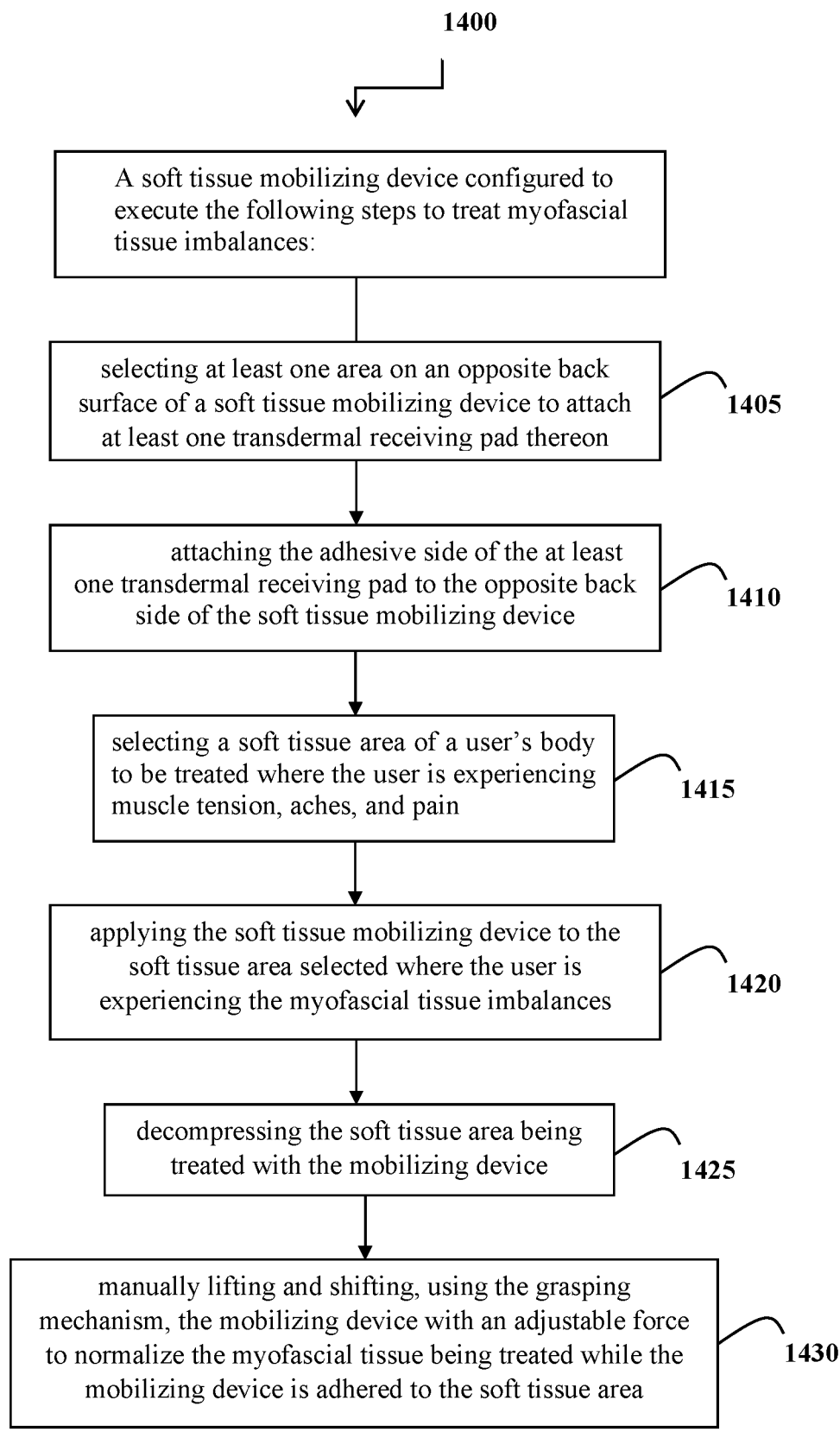

FIG. 14 represents an execution diagram for the method 1400 of using a soft tissue mobilizing device configured to treat myofascial tissue imbalances and/or reduce inflammation.

At block 1405, the method of the present invention comprises the step of selecting a soft tissue area of a user's or mammal's body to be treated where the user is experiencing muscle tension, aches, and pain.

At block 1410, the method comprises the step of applying a soft tissue mobilizing device to the soft tissue area selected where the user/mammal is experiencing the myofascial tissue imbalances. This step can also comprise the step of applying a soft tissue mobilizing device to the soft tissue area selected where the user/mammal is experiencing inflammation.

At block 1415, the method comprises the step of decompressing the soft tissue area being treated with the mobilizing device.

At block 1420, the method comprises the step of manually lifting and shifting, using the grasping mechanism, the mobilizing device with an adjustable force to normalize the myofascial tissue being treated while the mobilizing device is adhered to the soft tissue area.

The present invention can also include the step of applying a substance such a lotion, cream, gel and/or oil all having a chemical composition and/or an active ingredient of cannabinoid and/or terpene directly to a user's skin prior to applying the soft tissue device directly to the soft tissue area of a user's body.

Figure 15:
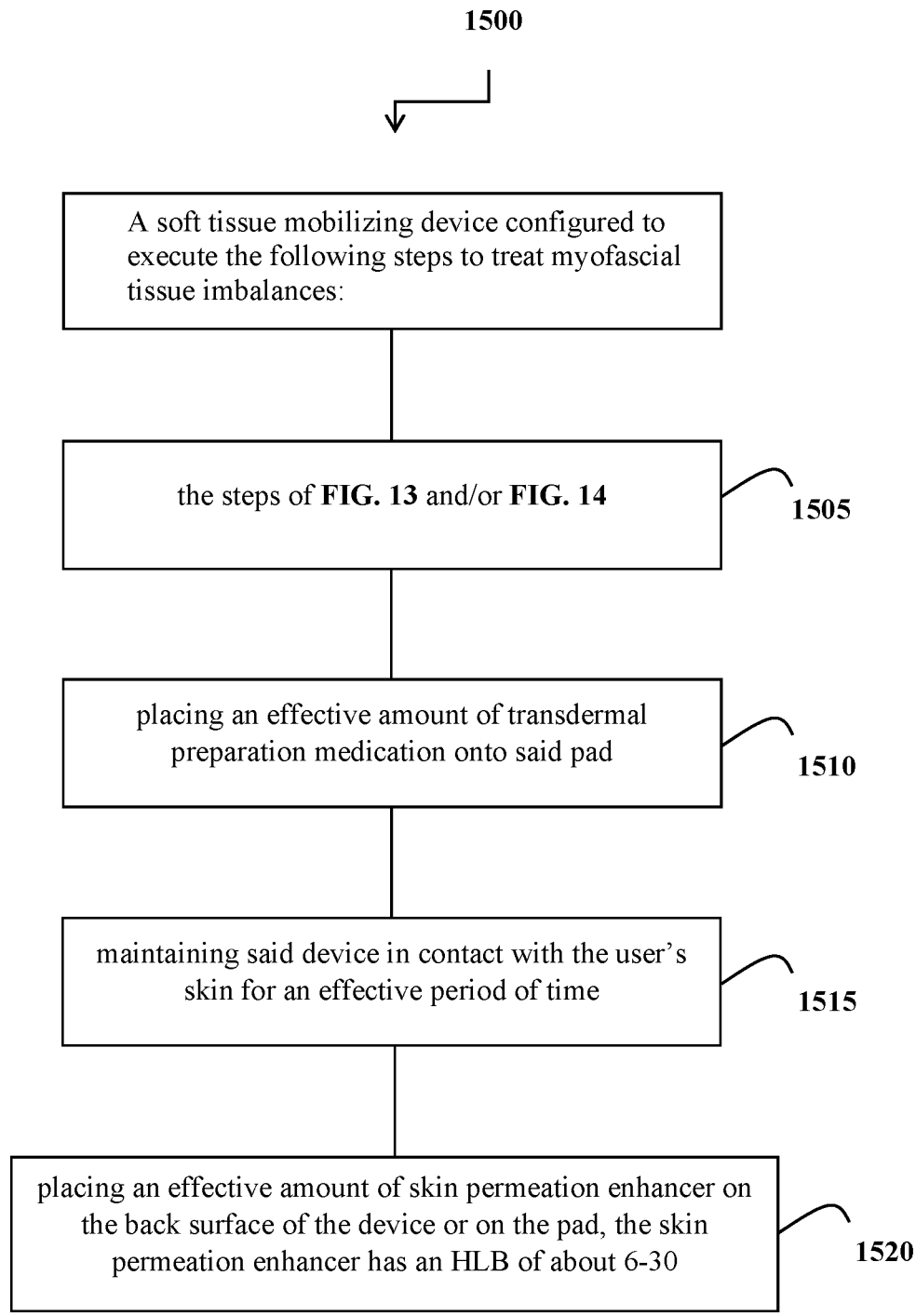

FIG. 15 represents an execution diagram for the method 1500 of using a soft tissue mobilizing device configured to treat myofascial tissue imbalances and/or treat inflammation.

At block 1505, the method comprises the step of selecting at least one area on an opposite back surface of a soft tissue mobilizing device to attach at least one transdermal receiving pad thereon.

At block 1510, the method of the present invention comprises the step of attaching the adhesive side of the at least one transdermal receiving pad to the opposite back side of the soft tissue mobilizing device.

At block 1515, the method of the present invention comprises the step of selecting a soft tissue area of a user's/mammal's body to be treated where the user/mammal is experiencing inflammation and/or muscle tension, aches, and pain.

At block 1520, the method of the present invention comprises the step of applying the soft tissue mobilizing device to the soft tissue area selected where the user/mammal is experiencing the myofascial tissue imbalances, pain and/or inflammation.

At block 1525, the method of the present invention comprises the step of decompressing the soft tissue area being treated with the mobilizing device.

At block 1530, the method of the present invention comprises the step of manually lifting and shifting, using the grasping mechanism, the mobilizing device with an adjustable force to normalize the myofascial tissue being treated while the mobilizing device is adhered to the soft tissue area.

The present invention can also include the step of applying a substance such a lotion, cream, gel and/or oil all having a chemical composition and/or an active ingredient of cannabinoid and/or terpene directly to a user's skin prior to applying the soft tissue device directly to the soft tissue area of a user's body FIG. 16 represents an execution diagram for the method 1600 of using a soft tissue mobilizing device configured to treat myofascial tissue imbalances and/or inflammation.

At block 1605, the steps of this embodiment are comprised of the method steps disclosed in FIG. 14 and/or FIG. 15.

At block 1610, the method of the present invention comprises the step of placing an effective amount of transdermal preparation therapeutic substance onto said pad.

At block 1615, the method of the present invention comprises the step of maintaining said device in contact with the user's skin for an effective period of time.

At block 1620, the method of the present invention comprises the step of placing an effective amount of skin permeation enhancer on the back surface of the device or on the pad, wherein the skin permeation enhancer has a hydrophilic-lipophilic balance (HLB) of about 8-18. In this disclosure, HLB refers to the hydrophilic-lipophilic balance of a surfactant which is a measure of the degree to which it is hydrophilic or lipophilic.

The present invention can also include the step of applying a substance such a lotion, cream, gel and/or oil all having a chemical composition and/or an active ingredient of cannabinoid and/or terpene directly to a user's skin prior to applying the soft tissue device directly to the soft tissue area of a user's body Direct Delivery (Topical Application)

In various embodiments, an effective amount of a therapeutic substance is placed directly on a select area of the user's skin. Once placed on the skin, a user/therapist/physician will let the therapeutic substance absorb into the skin for a predetermined amount of time. The therapeutic substance is configured to deliver an active ingredient (i.e., therapeutic or dietary supplement) of at least one terpene or one cannabinoid and/or a CBD derived from fruit, plants, vegetables, tree bark and/or a combination thereof through the skin and/or the myofascial and/or musculoskeletal tissue area of a user/mammal in order to help alleviate pain and to speed up the healing process.

Once the therapeutic substance has been on the user's skin for the predetermined amount of time, the back surface of the soft tissue device 1/11/21/31/41/51/61 is placed over the select area of the user's skin. After being placed on the user's skin, the soft tissue device will be used to decompress the soft tissue area being treated. Further, the mobilizing device will be manually lifted and shifted, using the grasping mechanism, with an adjustable force to normalize the myofascial tissue being treated while the mobilizing device is adhered to the soft tissue area.

In use, the back surface of the present invention includes an adhesive for allowing the device to be applied directly to a soft tissue area of a user's body where muscle tension, aches and pain are present. The applied device will also help to decompress the soft tissue area being treated.

CONCLUSION

As discussed herein, the therapy tape may be usable with human patients (e.g., children, adolescents, adults, elderly, and/or the like). Certain embodiments may be usable with animal patients (e.g., horses, cats, dogs, and/or the like). Moreover, as discussed herein, various embodiments of the present invention may be applied directly to a patient's skin. However, in various embodiments, therapy tape may be embedded within and/or on clothing (e.g., compression fit clothing, loose-fit clothing, smart clothing (e.g., having one or more network connected devices embedded therein), support devices (e.g., support sleeves, and/or the like), and/or the like.

It should be understood that the foregoing relates to exemplary embodiments of the invention and that modifications may be made without departing from the spirit and scope of the invention. It should also be understood that the present invention is not limited to the designs mentioned in this application and the equivalent designs in this description, but it is also intended to cover other equivalents now known to those skilled in the art, or those equivalents which may become known to those skilled in the art in the future.

INDUSTRIAL APPLICABILITY

The present invention pertains to a soft tissue mobilizing device having transdermal and/or topical delivery features for treating myofascial and musculoskeletal tissue imbalances to help alleviate pain, promote wellness and speed up the healing process, which may be of value and/or importance to various industries such as, but not limited to, the medical, physical therapy, sports medicine, athletic, sports, *cannabis*, or cosmetic industries.

What is claimed is:

1. An apparatus configured to treat myofascial tissue imbalances comprising:
   a soft tissue mobilizing device having a front surface and an opposite back surface;
   at least one transdermal receiving pad having medication disposed thereon that is adapted to be absorbed through a user's skin, wherein the at least one transdermal pad is coupled to the opposite back surface of the soft tissue mobilizing device, wherein the medication is at least one cannabinoid or at least one terpene, and wherein the cannabinoid or the terpene is comprised of an oil, a gel or a lotion;

wherein the front or back surface of the soft tissue mobilizing device is coupled to one or more transdermal stimulators arranged in cooperation thereof to stimulate transdermal features of the at least one transdermal receiving pad, thereby increasing a penetration and delivery rate of the medication, wherein the stimulator is a vibrator, a pressure applicator, or a transcutaneous electrical nerve stimulation device; and the front surface having a detachable grasping mechanism disposed thereon that allows a therapist or the user to grasp the grasping mechanism to manually lift and shift the device by hand via a flossing motion while the mobilizing device is adhered to a soft tissue area of the user being treated;

whereby the manual lifting and shifting of the user's soft tissue increases blood circulation around muscle and myofascial tissue of the user that helps to reduce a time period for normalizing the myofascial tissue area being treated, reduce a time period of alleviating muscle tension, aches, and pain of the user, and increase an absorption period of the medication through the user's skin.

2. The apparatus according to claim 1, wherein the at least one cannabinoid is selected from the group consisting of tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), and cannabicitran (CBT).

3. The apparatus according to claim 2, wherein the amount of CBD is in the range of 10 mg to 80 mg, and wherein the amount of THC is in the range of 2 mg to 25 mg.

4. The apparatus according to claim 1, wherein the medication is cannabidiol (CBD), wherein the CBD is a CBD derived from lemon peel, orange peel, tree bark or hops, and wherein the amount of CBD is in the range of 10 mg to 80 mg.

5. The apparatus according to claim 1, wherein the cannabinoid oil is comprised of water-soluble cannabinoid oil having particle diameters in the range of 3 to 100 nanometers.

6. The apparatus according to claim 2, wherein the CBD is a CBD derived from lemon peel, orange peel, tree bark or hops, and wherein the amount of the CBD is in the range of 10 mg to 165 mg.

7. The apparatus according to claim 2, wherein the amount of CBN is in the range of 10 mg to 35 mg.

8. The apparatus according to claim 1, wherein the at least one terpene is selected from the group consisting of myrcene, caryophyllene, limonene, linalool, pinene, and humulene.

9. The apparatus according to claim 8, wherein the amount of the myrcene is in the range of 5 mg to 125 mg, and wherein the myrcene is derived from fruits or herbs.

10. The apparatus according to claim 9, wherein the myrcene is derived from mangoes, basil, thyme, or lemongrass.

11. The apparatus according to claim 8, wherein the amount of the caryophyllene is in the range of 5 mg to 130 mg.

12. The apparatus according to claim 8, wherein the amount of the limonene is in the range of 10 mg to 90 mg.

13. The apparatus according to claim 12, wherein the limonene is derived from fruits or from citrus fruits.

14. The apparatus according to claim 8, wherein the amount of the linalool is in the range of 5 mg to 125 mg.

15. The apparatus according to claim 1, wherein the grasping mechanism is a gripping tab.

16. The apparatus according to claim 15, wherein the gripping tab is detachable.

17. The apparatus according to claim 16, wherein the gripping tab is pivotable.

18. An apparatus configured to treat myofascial tissue imbalances comprising:

a soft tissue mobilizing device having a front surface and an opposite back surface;

at least one transdermal receiving pad having medication disposed thereon that is adapted to be absorbed through a user's skin, wherein the at least one transdermal pad is coupled to the opposite back surface of the soft tissue mobilizing device, wherein the medication is at least one cannabinoid or at least one terpene, and wherein the cannabinoid or the terpene is comprised of an oil, a gel or a lotion;

wherein the front or back surface of the soft tissue mobilizing device is coupled to one or more transdermal stimulators arranged in cooperation thereof to stimulate transdermal features of the at least one transdermal receiving pad, thereby increasing a penetration and delivery rate of the medication, wherein the stimulator is a vibrator, a pressure applicator, or a transcutaneous electrical nerve stimulation device;

the back surface of the at least one transdermal receiving pad includes a skin permeation enhancer disposed thereon, wherein the skin permeation enhancer has a hydrophilic-lipophilic balance (HLB) of about 6-30; and the front surface having a grasping mechanism disposed thereon that allows a therapist or the user to grasp the grasping mechanism to manually lift and shift the device by hand via a flossing motion while the mobilizing device is adhered to a soft tissue area of the user being treated;

whereby the manual lifting and shifting of the user's soft tissue increases blood circulation around muscle and myofascial tissue of the user that helps to reduce a time period for normalizing the myofascial tissue area being treated, reduce a time period of alleviating muscle tension, aches, and pain of the user, and increase an absorption period of the medication through the user's skin.

* * * * *